(12) United States Patent
Swaniker

(10) Patent No.: US 9,808,554 B2
(45) Date of Patent: Nov. 7, 2017

(54) SUPER SOFT FOAMS

(71) Applicant: Covidien LP, Mansfield, MA (US)

(72) Inventor: Hansen P. Swaniker, Bristol, RI (US)

(73) Assignee: Covidien LP, Mansfield, MA (US)

( * ) Notice: Subject to any disclaimer, the term of this patent is extended or adjusted under 35 U.S.C. 154(b) by 143 days.

(21) Appl. No.: 14/336,229

(22) Filed: Jul. 21, 2014

(65) Prior Publication Data

US 2014/0330235 A1    Nov. 6, 2014

Related U.S. Application Data

(63) Continuation of application No. 11/700,063, filed on Jan. 31, 2007, now abandoned.

(60) Provisional application No. 60/763,730, filed on Jan. 31, 2006.

(51) Int. Cl.
| | |
|---|---|
| *A61L 26/00* | (2006.01) |
| *A61F 13/00* | (2006.01) |
| *C08G 18/10* | (2006.01) |
| *C08G 18/08* | (2006.01) |
| *C08G 18/28* | (2006.01) |
| *C08G 18/48* | (2006.01) |
| *C08G 18/64* | (2006.01) |
| *C08G 101/00* | (2006.01) |

(52) U.S. Cl.
CPC .... *A61L 26/0019* (2013.01); *A61F 13/00063* (2013.01); *A61L 26/0066* (2013.01); *A61L 26/0085* (2013.01); *C08G 18/10* (2013.01); *C08G 18/2825* (2013.01); *C08G 18/4833* (2013.01); *C08G 18/6484* (2013.01); *A61F 2013/0074* (2013.01); *A61F 2013/0091* (2013.01); *A61F 2013/00663* (2013.01); *A61F 2013/00676* (2013.01); *A61F 2013/00702* (2013.01); *A61F 2013/00927* (2013.01); *C08G 18/14* (2013.01); *C08G 2101/00* (2013.01); *C08G 2101/005* (2013.01)

(58) Field of Classification Search
CPC ..... C08G 18/10; C08G 18/6484; C08G 18/14
See application file for complete search history.

(56) References Cited

U.S. PATENT DOCUMENTS

| | | |
|---|---|---|
| 3,025,854 A | 3/1962 | Scholl |
| 3,156,242 A | 11/1964 | Crowe, Jr. |
| 3,285,245 A | 11/1966 | Eldredge et al. |
| 3,586,648 A | 6/1971 | Sambeth et al. |
| 3,598,122 A | 8/1971 | Zaffaroni |
| 3,797,494 A | 3/1974 | Zaffaroni |
| 3,903,232 A | 9/1975 | Wood et al. |
| 3,961,629 A | 6/1976 | Richter et al. |
| 3,978,855 A | 9/1976 | McRae et al. |
| 4,137,200 A | 1/1979 | Wood et al. |
| 4,339,550 A | 7/1982 | Palinczar et al. |
| 4,394,930 A | 7/1983 | Korpman |
| 4,622,089 A | 11/1986 | Lauritzen |
| 4,643,181 A | 2/1987 | Brown |
| 4,655,210 A | 4/1987 | Edenbaum et al. |
| 4,664,662 A | 5/1987 | Webster |
| 4,769,013 A | 9/1988 | Lorenz et al. |
| 4,860,737 A | 8/1989 | Lang et al. |
| 4,867,748 A | 9/1989 | Sauelsen |
| 4,960,594 A | 10/1990 | Honeycutt |
| 4,990,144 A | 2/1991 | Blott |
| 5,010,883 A | 4/1991 | Rawlings et al. |
| 5,060,642 A | 10/1991 | Gilman |
| 5,064,653 A | 11/1991 | Sessions et al. |
| 5,065,752 A | 11/1991 | Sessions et al. |
| 5,147,338 A | 9/1992 | Lang et al. |
| 5,149,469 A | 9/1992 | Komatsuzaki et al. |
| 5,328,450 A | 7/1994 | Smith et al. |
| 5,409,472 A | 4/1995 | Rawlings et al. |
| 5,429,591 A | 7/1995 | Yamamoto et al. |
| 5,466,462 A | 11/1995 | Rosenthal et al. |
| 5,512,041 A | 4/1996 | Bogart |
| 5,571,079 A | 11/1996 | Bello et al. |
| 5,571,080 A | 11/1996 | Jensen |
| 5,650,450 A | 7/1997 | Lovette et al. |
| 5,792,089 A | 8/1998 | Penrose et al. |
| 5,906,834 A | 5/1999 | Tseng |
| 5,968,542 A | 10/1999 | Tipton |
| 5,973,221 A | 10/1999 | Collyer et al. |
| 6,025,287 A | 2/2000 | Hermann |
| 6,117,437 A | 9/2000 | Roreger |
| 6,187,290 B1 | 2/2001 | Gilchrist et al. |
| 6,211,426 B1 | 4/2001 | Abrams |

(Continued)

FOREIGN PATENT DOCUMENTS

| | | | |
|---|---|---|---|
| BR | 9900032 A | * | 8/2000 |
| EP | 1493452 A2 | | 6/2004 |

(Continued)

OTHER PUBLICATIONS

Machine translation of p. 2, line 26—p. 3, line 5, and p. 3, lines 12-14 of BR 9900032 obtained from Google Translate on Jan. 6, 2017.*
Machine translation of abstract of BR 9900032 obtained from the European Patent Office website on Jan. 6, 2017.*
Examiner's First Report from counterpart Australian Patent Application No. 2007209923, dated Jan. 6, 2012, 2 pp.
Patent Examination Report No. 2 from counterpart Australian Patent Application No. 2007209923, dated Dec. 21, 2012, 3 pp.
Examiner's Report dated Feb. 11, 2013, from counterpart Canadian Patent Application No. 2637173, 5 pp.
Examiner's Report dated Nov. 13, 2013, from counterpart Canadian Patent Application No. 2637173, 2 pp.
Examination Report from counterpart European Patent Application No. 07709885.3, dated Mar. 26, 2013, 7 pp.

(Continued)

*Primary Examiner* — Melissa Rioja

(57) ABSTRACT

Super-soft foam materials, optionally for use as medical dressings, are provided. The pads are made of a foam prepared from NCO-terminated prepolymers in combination with an aqueous phase including fatty alcohols and alkyl polysaccharides. The foam may optionally contain at least one medicinal agent.

19 Claims, 9 Drawing Sheets

(56) References Cited

U.S. PATENT DOCUMENTS

| | | |
|---|---|---|
| 6,333,029 B1 | 12/2001 | Vyakarnam et al. |
| 6,420,623 B2 | 7/2002 | Augustine et al. |
| 6,486,378 B1 | 11/2002 | Areskoug et al. |
| 6,566,576 B1 | 5/2003 | Komerska et al. |
| 6,596,293 B1 | 7/2003 | Bootman et al. |
| 6,706,775 B2 | 3/2004 | Hermann et al. |
| 6,713,083 B1 | 3/2004 | McGregor et al. |
| 6,762,213 B2 | 7/2004 | Lejeune et al. |
| 6,803,495 B2 | 10/2004 | Simpson |
| 6,846,846 B2 | 1/2005 | Modak et al. |
| 6,888,042 B1 | 5/2005 | Freeman |
| 6,949,595 B2 | 9/2005 | Morgan et al. |
| 6,991,848 B2 | 1/2006 | Thomson |
| 7,045,673 B1 | 5/2006 | Batich et al. |
| 2001/0039324 A1 | 11/2001 | Sadvary et al. |
| 2002/0062097 A1 | 5/2002 | Simpson |
| 2003/0161758 A1 | 8/2003 | Whiteley |
| 2003/0186830 A1 | 10/2003 | Godtroid et al. |
| 2004/0086549 A1 | 5/2004 | Nielsen |
| 2004/0138605 A1 | 7/2004 | Sigurjonsson et al. |
| 2004/0153040 A1 | 8/2004 | Martineau et al. |
| 2004/0170670 A1 | 9/2004 | Smith et al. |
| 2004/0192547 A1 | 9/2004 | Wood et al. |
| 2004/0241206 A1 | 12/2004 | Ketelson et al. |
| 2005/0164898 A1 | 7/2005 | Kasturi et al. |
| 2005/0182347 A1 | 8/2005 | Bishop et al. |
| 2005/0222286 A1 | 10/2005 | Gilder et al. |
| 2005/0249791 A1 | 11/2005 | Hobbs et al. |
| 2005/0249818 A1 | 11/2005 | Sawan et al. |
| 2006/0129080 A1 | 6/2006 | Bjornberg et al. |
| 2006/0142529 A1 | 6/2006 | Thiede et al. |
| 2006/0142687 A1 | 6/2006 | Liedtke et al. |
| 2006/0258969 A1 | 11/2006 | Brown et al. |
| 2007/0020320 A1 | 1/2007 | David et al. |
| 2007/0055194 A1 | 3/2007 | Lerat et al. |
| 2007/0066920 A1 | 3/2007 | Hopman et al. |
| 2007/0066924 A1 | 3/2007 | Hopman et al. |
| 2007/0161936 A1 | 7/2007 | Svetlik |
| 2007/0185463 A1 | 8/2007 | Mulligan |
| 2010/0280427 A1* | 11/2010 | Larsen .................. A61L 15/26 602/46 |
| 2010/0286584 A1* | 11/2010 | Areskoug ........... A61F 13/0213 602/46 |

FOREIGN PATENT DOCUMENTS

| | | | |
|---|---|---|---|
| EP | 1488815 A1 | 12/2004 | |
| GB | 1429711 A * | 3/1976 | ............ A01C 1/044 |
| GB | 2406099 A | 3/2005 | |
| WO | WO 2005075001 A1 | 8/2005 | |

OTHER PUBLICATIONS

Supplementary Search Report from Counterpart European Patent Application No. 07709885.3, dated Nov. 17, 2009, 6 pp.
Examination Report from counterpart European Patent Application No. 07709885.3, dated Feb. 17, 2010, 1 pp.
Notice of Reasons for Rejection, and translation thereof, from counterpart Japanese Patent Application No. 2008553304, dated Nov. 29, 2013, 5 pp.
Prosecution History from U.S. Appl. No. 11/700,063, dated Oct. 23, 2008 through Jun. 9, 2014, 260 pp.
Examination Report from counterpart Indian Application No. 6718/DELNP/2008, dated Jul. 11, 2016, 6 pp.

* cited by examiner

SUPER SOFT FOAMS

CROSS-REFERENCE TO RELATED APPLICATIONS

This application is a continuation of, and claims the benefit of and priority to, U.S. patent application Ser. No. 11/700,063 filed Jan. 31, 2007, which, in turn, claims the benefit of and priority to U.S. Provisional Patent Application No. 60/763,730, filed Jan. 31, 2006, the entire disclosures of each of which are incorporated by reference herein.

BACKGROUND

The present disclosure relates to foams. According to certain embodiments, the foams are suitable for use as wound dressings. The foams have both excellent softness characteristics and fluid management capabilities. The use of absorbent pads in wound dressings is known. Such pads protect the wound and provide both cushioning to the wound site and assist in the collection of exudate from the wound. Such absorbent pads may also be used as medical products, such as diapers, sanitary napkins, bandages, and the like.

Foams utilized to form absorbent pads have been made are also known. For example, U.S. Pat. No. 4,394,930 discloses such an absorbent foam product. Polyurethane foams also known. See, for example, U.S. Pat. Nos. 3,586,648 and 3,903,232. Also relevant are the foams of U.S. Pat. Nos. 3,961,629, 4,664,662, 4,339,550, and 5,065,752.

Despite the wide variety of known absorbent pads and polyurethane foam compositions, there still remains a need for absorbent foam compositions which have desirable softness and liquid retaining characteristics.

SUMMARY

The present disclosure provides foams including at least one NCO-terminated hydrophilic urethane prepolymer formed from at least one isocyanate in combination with a polyether polyol including a polyalkylene oxide and a compound containing at least two active hydrogen atoms such as a polyhydric alcohol, polyhydric phenol, amine, polycarboxylic acid, and phosphorous acid. The foam also includes an aqueous phase including deionized water, at least one fatty alcohol, and at least one alkyl polysaccharide.

The present disclosure also provides foams including at least one NCO-terminated hydrophilic urethane prepolymer including at least one isocyanate such as an aromatic isocyanate, aliphatic isocyanate, and combinations thereof in combination with a polyether polyol including an alkylene oxide and a compound containing at least two active hydrogen atoms such as a polyhydric alcohol, polyhydric phenol, amine, polycarboxylic acid, and phosphorous acid. The foam also includes an aqueous phase including deionized water, at least one fatty alcohol such as caproic alcohol, caprylic alcohol, 2-ethylhexyl alcohol, capric alcohol, lauryl alcohol, isotridecyl alcohol, myristyl alcohol, cetyl alcohol, hexyl decanol, palmitoleyl alcohol, stearyl alcohol, cetearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, octyl dodecanol, erucyl alcohol brassidyl alcohol, coconut oil, cetearyl alcohol, behenyl alcohol, and combinations thereof, and at least one alkyl polysaccharide of the formula:

$$RO(C_nH_{2n}O)_r(Z)_x \qquad (I)$$

wherein Z is derived from glucose, R is a hydrophobic group such as alkyl, alkylphenyl, hydroxyalkylphenyl, and mixtures thereof having from about 10 to about 18 carbon atoms, n is from about 2 to about 3, r is from about 0 to about 10, and x is from about 1.5 to about 8.

Foams of the present disclosure may be utilized as medical products, such as diapers, sanitary napkins, and dressings for wounds. In embodiments, the foams may be applied to a backing layer for use as a dressing. Where a foam of the present disclosure is utilized with a backing layer, an adhesive may be present to enhance adherence of the foam to the backing layer and/or any substrate to which the dressing may be applied.

The foams may also include a medicinal agent or other additive. In certain embodiments, the foam may include an antimicrobial agent as a medicinal agent. In some embodiments, the antimicrobial agent is PHMB, or a derivative thereof such as PEHMB. Where the foam is utilized as a dressing, any other layer of the dressing, such as a backing layer and/or an adhesive layer, may also include a medicinal agent or other additive.

According to a further aspect of the present invention, there is provided a method of reducing the count of one or more pathogens comprising: identifying a source of exudate containing one or more pathogens, applying a medical product comprising the foam of the present invention to the source, absorbing exudate into the foam, and killing pathogens contained in the exudate absorbed into the foam, thereby rendering cleaned exudate.

DETAILED DESCRIPTION

Figure 1A:
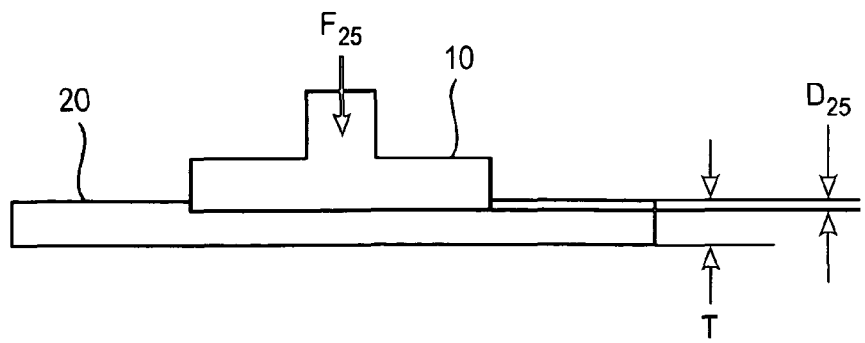
FIG. 1A is a depiction of an apparatus which may be utilized to determine the Indentation Force Deflection (IFD) of a foam by indenting the foam 25%.

The foam compositions of the present disclosure include NCO-terminated polyether prepolymers in combination with an aqueous phase possessing alcohol and polysaccharide surfactants. At least one NCO-terminated prepolymer is rapidly polymerized in an aqueous phase including surfactants, resulting in the formation of a foam of the present disclosure. In embodiments, at least one may be from about one to about twenty and, in embodiments, from about two to about ten. The foam of the present disclosure, in turn, may be used to form a wound dressing, including a super soft pad for use as a wound dressing.

Polyether prepolymers which may be utilized to form the compositions of the present disclosure include hydrophilic polyether polyols. Illustrative of suitable hydrophilic polyether polyols include the reaction product of ethylene oxide or combinations of ethylene oxide with other alkylene oxide(s) with one or more compounds containing at least two active hydrogen atoms, such as polyhydric alcohols, polyhydric phenols, amines, polycarboxylic acids, phosphorous acids and the like. Suitable examples of polyhydric alcohols include dihydric alcohols, such as ethylene glycol, propylene glycol, 1,3- and 1,4-butanediols, 1,6-hexanediol, diethylene glycol, bis(hydroxymethyl)cyclohexane, bis(hydroxyethyl)benzene, hydrogenated bisphenol A, hydrogenated bisphenol F, polytetramethylene glycols, polyester diols and silanol-terminated polysiloxanes; trihydric alcohols, such as glycerol, trimethylol propane, trimethylol ethane, 1,2,3-butane triol, 1,2,6-hexane triol and polyester triols; and polyhydric alcohols having 4 to 8 or more hydroxyl groups, such as pentaerythritol, diglycerol, α-methylglucoside, sorbitol, xylitol, mannitol, glucose, fructose, sucrose, and the like. Exemplary of suitable polyhydric phenols are mono- and polynuclear phenols, such as hydroquinone, catechol, resorcin, pyrogallol, and bisphenols (bisphenol A, bisphenol F, bisphenol S, and the like), as well as phenol-formaldehyde condensation products. Suitable amines include ammonia; alkanol amines, such as mono-, di- and tri-ethanol amines, isopropanol amines and the like; aliphatic, aromatic, araliphatic and alicyclic monoamines, such as $C_1$ to $C_{20}$ alkyl amines (methyl-, ethyl-, isopropyl-, butyl-, octyl-, and laurylamines, and the like), aniline, toluidine, naphthylamines, benzylamine, cyclohexylamine and the like, aliphatic, aromatic, alicyclic and araliphatic polyamines, such as $C_2$ to $C_6$ alkylene diamines (such as ethylene diamines), diethylene triamine, tolylene diamines, phenylene diamines, xylylene diamines, methylene diamines, diphenylether diamines, isophorone diamine, cyclohexylene diamines, dicyclohexylmethane diamines and the like; and heterocyclic polyamines, such as piperazine, N-aminoethyl-piperazine, and other heterocyclic polyamines.

Suitable alkylene oxides which may be employed in combination with ethylene oxide for producing polyether polyols include, for example, propylene oxide, 1,2-, 2,3-, 1,3-, and 1,4-butylene oxides, styrene oxide, epichlorohydrin and the like, as well as combinations of two or more of them.

The addition of ethylene oxide or the combination thereof with alkylene oxide to the active hydrogen atom-containing compounds can be carried out in any conventional manner, with or without catalysts, such as alkaline catalysts, amine catalysts, or acidic catalysts, under normal or elevated pressure, in a single step or in a multi-stage process. The addition of ethylene oxide and alkylene oxide may be performed by random-addition, block-addition or a combination thereof, for example random addition followed by block addition. Random addition may be utilized in some embodiments.

In embodiments, polyols used for producing the NCO-terminated prepolymer may have an oxyethylene content suitably of at least about 30%, in embodiments from about 50% to about 90% by weight, and from about 2 to about 8 hydroxyl groups (average), in embodiments from about 2 to about 4 hydroxyl groups.

The polyether polyols described above are then capped with isocyanates such as aromatic isocyanates or aliphatic isocyanates. Suitable aromatic isocyanates include those containing from about 6 to about 20 carbon atoms, not including the carbon atoms in the NCO groups. Specific examples include, but are not limited to, p-phenylene diisocyanate (PDI), 4,4'-diphenylmethane diisocyanate (MDI) and position isomers thereof, 2,4- and/or 2,6-toluene diisocyanate (collectively TDI) and position isomers thereof, 3,4-dichlorophenyl diisocyanate, dicyclohexylmethane-4,4'-diisocyanate (HMDI), 1,6-hexamethylene diisocyanate (HDI) and position isomers thereof, and the like. Suitable aliphatic isocyanates include isophorone diisocyanate (IPDI) and the like.

In reacting the isocyanates with at least one hydrophilic polyether polyol to form NCO-terminated hydrophilic urethane prepolymers, the ratio of NCO/OH may be from about 1.5 to about 5.0, in embodiments from about 1.7 to about 3.0. The reaction of the isocyanate with the polyether polyol to form the prepolymer can be performed in any conventional manner. In some embodiments the reaction may be carried out in the presence of a catalyst.

The NCO-content of the present NCO-terminated hydrophilic prepolymers may be from about 1 to about 10% by weight, in embodiments from about 2 to about 8% by weight.

Suitable NCO-terminated polyether prepolymers for use in accordance with the present disclosure are within the purview of one skilled in the art and include, for example, the prepolymers disclosed in U.S. Pat. Nos. 3,903,232 and 4,137,200. Such prepolymers may have an average isocyanate functionality of greater than 2, in embodiments from about 2 to about 10. In embodiments, suitable NCO-terminated polyether prepolymers include those sold under the trademark HYPOL, such as HYPOL 2000, HYPOL 2002, HYPOL 3000, HYPOL 4000, HYPOL 5000, HYPOL X6100 and HYPOL hydrogel.

Suitable NCO-terminated polyether prepolymers may have an equivalent weight (molecular weight per NCO group) of from about 100 to 1,000 daltons, in embodiments from about 500 to about 750 daltons; an NCO content of from about 1.3 meq/g to about 1.8 meq/g, in embodiments from about 1.5 meq/g to about 1.6 meq/g; a viscosity of from about 16,000 cps to about 21,000 cps, in embodiments from about 18,000 cps to about 20,000 cps; less than about 3% by weight free TDI, in embodiments from about 0.1% to about 3% by weight free TDI; from about 0.3 to about 1.7% by weight free MDI, in embodiments from about 0.5 to about 1.5% by weight free MDI; and a specific gravity of from about 1 g/cm$^3$ to about 1.3 g/cm$^3$, in embodiments from about 1.1 g/cm$^3$ to about 1.2 g/cm$^3$.

In some embodiments, HYPOL 2002 may be utilized as the NCO-terminated polyether prepolymer. HYPOL 2002 has an equivalent weight (molecular weight per NCO group) of about 633 daltons, an NCO content of about 1.58 meq/g, a viscosity of about 19,000 cps, less than about 3% by weight free TDI, from about 0.7 to about 1.3% by weight free MDI, and a specific gravity of about 1.19 g/cm$^3$.

The NCO-terminated polyether prepolymer may then be combined with an aqueous phase to produce a foam of the present disclosure. In embodiments the aqueous phase may be water, including deionized water. The aqueous phase may also include surfactants including, but not limited to, alcohols, polysaccharides, combinations thereof, and the like.

In embodiments, suitable alcohols which may be added to the aqueous phase include fatty alcohols. Suitable fatty alcohols include caproic alcohol, caprylic alcohol, 2-ethylhexyl alcohol, capric alcohol, lauryl alcohol, isotridecyl alcohol, myristyl alcohol, cetyl alcohol, hexyl decanol, palmitoleyl alcohol, stearyl alcohol, cetearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, octyl dodecanol, erucyl alcohol and brassidyl alcohol and the technical mixtures thereof obtained, for example, in the high-pressure hydrogenation of technical methyl esters based on fats and oils or aldehydes from Roelen's oxo synthesis and as monomer fraction in the dimerization of unsaturated fatty alcohols. In some embodiments the fatty alcohols may include technical $C_{12-18}$ fatty alcohols such as, for example, coconut oil, cetearyl alcohol, or behenyl alcohol. A single fatty alcohol may be used or any combination of fatty alcohols may be used.

In embodiments, an ether may also be added to the aqueous phase for use as a surfactant. Where present, ethers may be included in combination with other ethers or in combination with fatty alcohols as described above. Suitable ethers include alcohol polyglycol ethers. Alcohol polyglycol ethers may be the adducts of on average from about 5 to about 40 mol, in embodiments from about 10 to about 30 mol, ethylene oxide with caproic alcohol, caprylic alcohol, 2-ethylhexyl alcohol, capric alcohol, lauryl alcohol, isotridecyl alcohol, myristyl alcohol, cetyl alcohol, hexyl decanol, palmitoleyl alcohol, stearyl alcohol, cetearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, octyl dodecanol, behenyl alcohol, erucyl alcohol and brassidyl alcohol and technical mixtures thereof. In embodiments, mixtures of adducts of from about 10 to about 12 mol and from about 15 to about 20 mol, respectively, of ethylene oxide with cetearyl alcohol may be utilized.

In embodiments, EMULGADE® 1000 NI from Cognis Corporation (Ambler, Pa.) may be utilized as the alcohol. EMULGADE® 1000 NI is a mixture of cetearyl alcohol and ceteareth-20 (polyoxyethylene cetyl/stearyl ether).

In embodiments, suitable polysaccharides which may be added to the aqueous phase include alkyl polysaccharide surfactants which are within the purview of one skilled in the art. The alkyl polysaccharides which can be used may have a hydrophobic group containing from about 8 to about 20 carbon atoms, in embodiments from about 10 to about 16 carbon atoms, typically from about 12 to about 14 carbon atoms, and polysaccharide hydrophilic group containing from about 1.5 to about 10, in embodiments from about 1.5 to about 4, typically from about 1.6 to about 2.7 saccharide units (e.g., galactoside, glucoside, fructoside, glucosyl, fructosyl; and/or galactosyl units). Mixtures of saccharide moieties may be used in the alkyl polysaccharide surfactants.

Suitable alkyl polysaccharides include decyl, dodecyl, tetradecyl, pentadecyl, hexadecyl, and octadecyl, di-, tri-, tetra-, penta-, and hexa-, glucosides, galactosides, lactosides, fructosides, fructosyls, lactosyls, glucosyls and/or galactosyls and mixtures thereof.

In embodiments, suitable alkyl polyglucosides which may be utilized may have the following formula: $RO(C_nH_{2n}O)_r(Z)_x$ (I); wherein Z is derived from glucose, R is a hydrophobic group such as alkyl, alkylphenyl, hydroxyalkylphenyl, and mixtures thereof, in which said alkyl groups contain from about 10 to about 18, in embodiments from about 12 to about 14 carbon atoms; n is from about 2 to about 3; r is from about 0 to about 10; and x is from about 1.5 to about 8, in embodiments from about 1.5 to about 4, typically from about 1.6 to about 2.7.

To prepare these compounds, a long chain alcohol ($R_2OH$, where $R_2$ is an alkyl group of from about $C_{10}$ to about $C_{18}$) can be reacted with glucose, in the presence of an acid catalyst, to form the desired glucoside. Alternatively, the alkyl polyglucosides can be prepared by a two step procedure in which a short chain alcohol ($R_1OH$ wherein $R_1$ is an alkyl having from about 1 to about 6 carbon atoms) may be reacted with glucose or a polyglucoside (x=2 to 4) to yield a short chain alkyl glucoside (x=1 to 4) which can in turn be reacted with a longer chain alcohol ($R_2OH$) to displace the short chain alcohol and obtain the desired alkyl polyglucoside. If this two step procedure is used, the short chain alkylglucoside content of the final alkyl polyglucoside material should be less than about 50%, in embodiments less than about 10%, typically less than about 5%, in embodiments about 0% of the alkyl polyglucoside.

The amount of unreacted alcohol (the free fatty alcohol content) in the desired alkyl polysaccharide surfactant may be less than about 2%, in embodiments less than about 0.5% by weight of the total of the alkyl polysaccharide. For some uses it may be desirable to have the alkyl monosaccharide content less than about 10%.

As used herein, an "alkyl polyglucoside" includes alkyl polyglycosides because the stereochemistry of the saccharide moiety is changed during the preparation reaction.

In some embodiments, the glycoside surfactant may be an alkyl polyglucoside such as GLUCOPON® 625 manufactured by the Cognis Corporation (Ambler, Pa.).

The pH of the aqueous phase may be adjusted to a desired level to enhance the formation of the foams of the present disclosure. The pH of the aqueous phase may range from about 4 to about 8, and in certain exemplary embodiments, a pH of about 6 to about 7 may be utilized.

Fatty alcohols, alcohol polyglycol ethers and/or alkyl polysaccharides may be added alone or in any combination to the aqueous phase. In embodiments, once formed, the aqueous phase may be contacted with the NCO-terminated prepolymers described above for formation of a foam of the present disclosure.

Various methods may be utilized to form the foams of the present disclosure. For example, either a one-shot process or a prepolymer process can be used. In the one-shot process, all the components, that is the polyether polyol, isocyanate, aqueous phase including any surfactants described herein and, where appropriate, fillers and additives and any other components may be combined all at once. In the prepolymer process, an NCO-terminated prepolymer is initially prepared as described above, and then added to the aqueous phase and, where appropriate, fillers and additives and any other components may be combined all at once. Methods for combining the components of the foam of the present disclosure are within the purview of one skilled in the art and include, for example, mixing, blending, and the like.

In these procedures it is possible for the conveyance, metering and mixing and foaming of the individual components and of the other components or component mixtures to take place with equipment within the purview of one skilled in the art.

The properties of the resulting foam of the present disclosure may be modified by varying the OH/NCO ratio, that is, the ratio of the aqueous phase to the NCO-terminated prepolymer. The ratio of aqueous phase to NCO-terminated prepolymer may be from about 1:1 to about 3:1, in embodiments from about 1.3:1 to about 2:1, with a ratio of about 1.5:1 being used in some embodiments.

The foams can be mixed for a time from about 0.5 to about 30 minutes, in embodiments from about 1 minute to about 15 minutes. After mixing, the foams can be poured out or spread out to form sheet-like structures. Foam thicknesses of from about 0.015 mm to about 15 cm can be obtained without difficulty in this way. The thickness of material depends on the purpose of use: if a large amount of liquid is to be absorbed per unit area, a correspondingly thick foam material should be spread. If only a small volume of liquid is to be managed per unit area, very thin layers may be sufficient. Thin applications of composition as far as 10 g/m$^2$ can easily be produced in the spreading. However, it is also possible and advantageous to fabricate from the foams according to the present disclosure articles which are not sheet-like but markedly space-filling, for example by customary casting processes.

In embodiments, the sheet-like structures may be referred to as a pad and, because of the enhanced properties exhibited by the foams of the present disclosure, in embodiments the pads may be referred to as super soft pads.

The resulting foam may then be dried. Methods for drying are within the purview of those skilled in the art and include, for example, heating such as by forced air or in an oven, the use of radiofrequency radiation, and the like. In embodiments, radiofrequency radiation may be advantageously used to form a foam of the present disclosure. The resulting foams may be sterilized by any suitable method including, for example, gamma irradiation, electron beam sterilization, ethylene oxide sterilization, combinations thereof, and the like.

The foams according to the present disclosure can also be applied by processes within the purview of those skilled in the art to sheet-like backings, for example woven, knitted, nonwoven fabrics or sheets. The present disclosure likewise relates to the resulting products. One side of the backing is typically provided with a polyurethane foam layer according to the present disclosure. The foam of the present disclosure may be coextensive with the backing layer. In other embodiments, the foam of the present disclosure may be a pad covered by a backing layer that is larger than the circumference of the pad.

The backing materials utilized in these sheet-like structures may have a wide variety of origins, that is to say materials based on natural, semisynthetic or completely synthetic raw materials, and of organic or inorganic origin can be used. It is possible to use, for example, plastic and metal sheets, mats, nonwoven, knitted or woven fabrics of organic or inorganic fiber material, paper and foam sheets or also combinations of these backing materials. Sheet-like structures which are permeable to air and moisture may be suitable for medical use, for example micro- and macroporous plastic sheets and nonwoven fabrics, and elastic textile backing materials, especially stretch fabrics, and gauze bandages.

The present disclosure also includes processes for the production of sheet-like structures based on backing materials coated with foams of the present disclosure; the process is characterized in that the foams defined above or reaction mixtures able to form foams are applied to the surface of a backing material, for example by direct processes or reverse processes by casting or knife application, with the backing material surface being, where appropriate, only partially covered by the foam. The layer thickness of the foam can be, for example, from about 0.015 mm to about 150 mm, in embodiments from about 0.1 mm to about 50 mm, typically from about 0.1 mm to about 6 mm.

The sheet-like structures according to the present disclosure can be produced continuously or batchwise. The procedure depends on the given sheet-like structures to be provided. A batchwise procedure is often advantageous when backing materials which have already been cut out are available. The continuous procedure may be suitable for applications where no backing material is present or for coating backing materials which are available in continuous form, for example as rolled material. The application of the foam to the backing material can in this case take place directly or by the reverse process. The reaction mixture can also be applied by knife in the said processes before it solidifies due to the reaction.

In embodiments, it may be useful to treat the foams and backing materials according to the present disclosure by irradiation with gamma rays, by corona treatments, or similar treatments, to improve the cohesion of the foam to any backing material.

In embodiments, the backing layer may also be coated with a customary adhesive composition such as a pressure sensitive adhesive to both enhance adherence of the backing layer to the foam and adherence of the backing layer to skin or any other substrate to which it may be applied. Any medically accepted, skin friendly adhesive is suitable, including acrylic, hydrocolloid, hydrogel, polyurethane and silicone based adhesives.

In other embodiments, a dressing of the present disclosure may include an island of foam on a backing layer, wherein at least the marginal portions of the backing layer are coated with adhesive. The adhesive may be applied either continuously or discontinuously over the marginal portions of the backing layer.

In embodiments, foams according to the present disclosure may be applied to backings composed of polyurethane sheets and utilized as wound dressings. Backing sheets of this type may have thicknesses of from about 5 to about 200 µm, in embodiments from about 10 to about 100 µm, typically from about 15 to about 70 µm. The values for the permeability to water vapor may be from about 500 to about 10,000 g/m²/24 h, in embodiments from about 700 to about 7000 g/m²/24 h, typically from about 1000 to about 5000 g/m²/24 h.

In embodiments, the backing layer may include a polyurethane sheet as described above, optionally in combination with other layers. For example, additional synthetic materials may be utilized in combination with a polyurethane to form a multi-layer backing material for use with the foams of the present disclosure. Suitable additional synthetic materials include, but are not limited to, acetate fibers, acrylic fibers, cellulose ester fibers, modacrylic fibers, polyamide fibers, polyester fibers, polyolefin fibers, polyvinyl alcohol fibers, rayon fibers, polyethylene foam, and combinations thereof. In embodiments, fibers such as nylon fibers, rayon fibers, polyolefin fibers, polyester fibers, and combinations thereof may be utilized as an additional layer of the backing material. Suitable polyolefin fibers include those of polyethylene, polypropylene, polybutylene, polypentene, and combinations and copolymers thereof. Suitable polyester fibers include polyethylene terephthalate, polybutylene terephthalate, polycyclohexylenedimethylene terephthalate, and combinations and copolymers thereof.

Other layers which may be utilized in combination with the polyurethane backing layer described above include nonwoven materials such as combinations of layers of random and carded fibers. The fibers may be of natural or synthetic origin. Natural fibers which may be utilized in nonwoven materials include silk fibers, keratin fibers such as wool fibers, camel hair fibers, and the like, and cellulosic fibers including wood pulp fibers, cotton fibers, hemp fibers, jute fibers, flax fibers, and mixtures thereof. Synthetic fibers which may be utilized in nonwoven materials include acetate fibers, acrylic fibers, cellulose ester fibers, modacrylic fibers, polyamide fibers, polyester fibers, polyolefin fibers, polyvinyl alcohol fibers, rayon fibers, and mixtures thereof.

The nonwoven layer may be prepared by a variety of processes including hydroentanglement, air entanglement, thermally bonding or thermo-bonding, and combinations of these processes.

In embodiments, the backing layer may possess a multi-layer configuration including, but not limited to, thermoplastic polyurethanes such as the PELLETHANE® thermoplastic polyurethanes from Dow Chemical Co. (Midland, Mich.) in combination with other materials, including polyethylene terephthalate (PET), and nonwoven layer materials including hydroentangled materials containing about 50% rayon and 50% polyester sold under the trade name HEF by Veratec, Inc. (Walpole, Mass.). The layers making up such a multi-layer configuration may be in any order.

The present disclosure also relates to the use of the foams according to the present disclosure in medicine, for example for the treatment of defect wounds or for the prophylaxis thereof, in particular as wound dressings, bandages or supports, and as protection and padding material, in particular for prophylaxis.

Wound dressings including the foams of the present disclosure possess excellent mechanical and wound-healing properties. For example, in embodiments, foams of the present disclosure possess excellent indentation force deflection. Indentation Force Deflection (IFD) is a measurement of foam firmness or softness and is indicative of the surface feel of the foam. It is measured by indenting the foam 25% of its original height. A depiction of an apparatus utilized to measure IFD is set forth in FIG. 1A. As seen in FIG. 1A, indentor foot 10 is used to indent specimen 20 by 25% $D_{25}$ of its thickness T. The force required to achieve 25% indentation $F_{25}$ is measured and divided by the specimen's thickness T to obtain its softness value. The lower the force value, the softer the foam, and the more supple the surface feels.

To facilitate comparison of pads with different thicknesses, it may be desirable to normalize the IFD data by dividing the IFD 25% by the thickness of the pad sample tested.

Figure 1B:
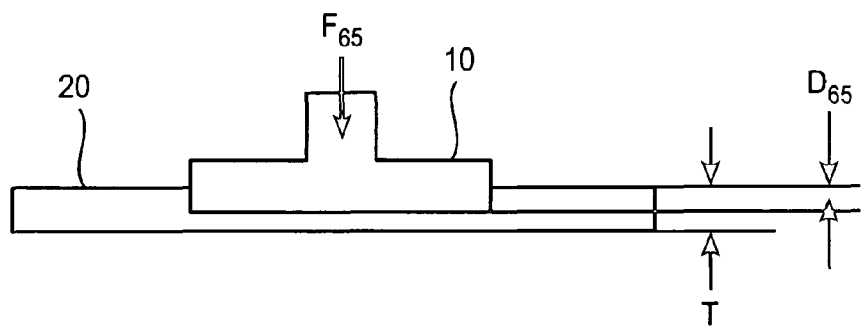
FIG. 1B is a depiction of an apparatus which may be utilized to determine the Indentation Force Deflection (IFD) of a foam by indenting the foam 65%.

A second IFD measurement may be taken by indenting the foam 65% $D_{65}$ of its original thickness T. This second IFD measurement is used to help determine the ability of the foam to provide support. A depiction of such a test is set forth in FIG. 1B. As set forth in FIG. 1B, indentor foot 10 is used to indent specimen 20 by 65% $D_{65}$ of its thickness T. The force required to achieve 65% indentation $F_{65}$ is measured and divided by the force required to achieve 25% deflection $F_{25}$ to obtain the support factor value for the specimen. Generally, the greater the difference between the 25% IFD and the 65% IFD, the more ability the foam has to support weight. The ratio of the 65% IFD to the 25% IFD is called the foam's support factor. Support factors for currently available foams can be from about 1.5 to about 2.6. The higher the number, the better the ability of the foam to provide support.

Currently available super-soft foams typically have IFD 25% of around 10 pounds. Foams with IFD 25% below 10 pounds tend to have compromised support factors around the low end of the acceptable range (about 1.5), in some cases less than about 1.5.

To the contrary, foams of the present disclosure may be utilized to form super-soft polymeric dressing pads, in embodiments a polyurethane foam pad, having an IFD 25% of from about 1 pound (4.4N) to about 2 pounds (8.9N) and an IFD 65% of from about 3.5 pounds (16N) to about 9 pounds (40N). The foam pads of the present disclosure also possess a support factor that is from about 3.5 to about 4.5, which is significantly higher than the support factor of currently available pads which, as noted above, is from about 1.5 to about 2.6.

Figure 1C:
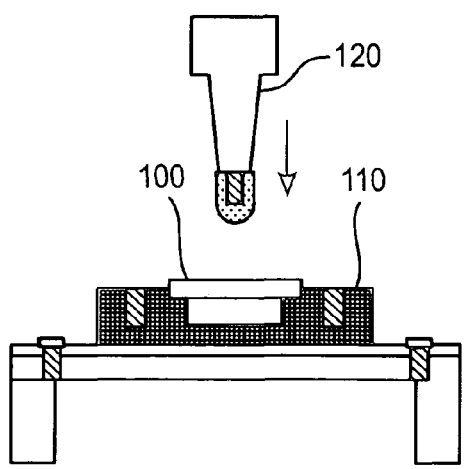
FIG. 1C is a depiction of an apparatus which may be utilized to determine the conformability of a foam of the present disclosure, that is, the measure of the flexural rigidity or the resistance to bending of the foam.
Figure 1D:
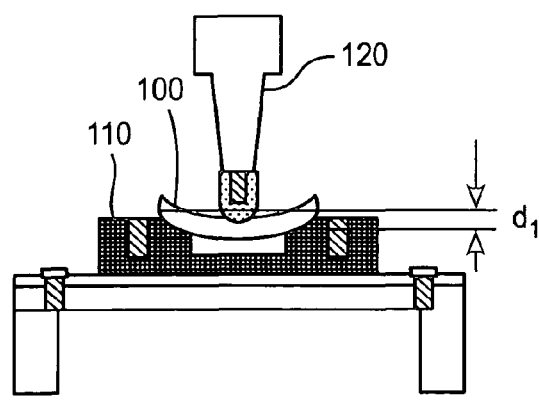
FIG. 1D is a depiction of the apparatus of FIG. 1C in use.

Foams of the present disclosure may also be utilized to form pads for use as dressings with superior conformability. Conformability is used herein as the measure of the flexural rigidity or the resistance to bending of a material. It may be measured utilizing an apparatus as depicted in FIG. 1C. The test specimen 100 is placed in a sample holder 110 and is supported on all four sides in the test sample holder 110. An unknown force (F), directed through the center of the test specimen is applied in a direction perpendicular to the surface of test sample using force arm 120. The maximum force required to bend or flex a test specimen a distance $d_1$ of 1 cm is measured. FIG. 1D shows the apparatus in use wherein the test specimen has been flexed a distance $d_1$ of 1 cm. The measured force is then divided by the volume of the specimen tested to obtain Force/Unit volume, which is the measure of the conformability of the specimen tested.

Currently available foam dressing pads possess conformability values of from about 0.1N/cm³ to about 0.3 N/cm³. To the contrary, foam pads prepared with foams of the present disclosure possess much lower conformability values, which can be from about 0.01 N/cm³ to about 0.1N/cm³, in embodiments from about 0.03 N/cm³ to about 0.05 N/cm³.

The foams of the present disclosure possess a dense network of cells that may be utilized to form a super soft pad for use as a dressing. The dense network of cells creates a tortuous path for fluid flow within the pad such that, in the absence of artificially exerted forces, fluids absorbed into the pad matrix are retained within its structure. To the contrary, currently available foam pads use secondary methods, such as lamination of films to one or both sides of the pad, to achieve the same feature.

To avoid leakage in the presence of artificially exerted forces, it may be desirable to utilize unidirectional films to facilitate fluid retention within the pad matrix. Such unidirectional films include the backing layers/films described above.

Foams of the present disclosure also possess desirable fluid management characteristics.

The following Table 1 summarizes some of the beneficial properties of the foam material of the present invention, and compares these properties with similarly measured properties possessed by commercially available wound care products. The values contained therein represent the average value of 10 tests for each parameter measured.

grams. A bath is filled with saline solution, and each of the samples is placed in the saline bath. Using a plate, the sample is compressed and released inside the saline bath three times in succession to remove any air bubbles which may be trapped within the sample, and to force fluid into the matrix of the sample. The samples are allowed to sit in the saline bath for a minimum of 12 hours. A petri dish is placed on a scale, and the scale is tared-out. The sample is quickly transferred from the saline bath to the petri dish, and the wet weight (ww) is measured and recorded. The sample is then transferred to another petri dish which they're from, and the dish containing the sample is then rocked in the palm of the hand until there is no more fluid dripping from the specimen, or there is less than one drop every 10 seconds coming off the sample. The sample is then reweighed (rw) and its weight recorded. The fluid capacity (fc) is calculated as follows: $fc=ww-dw/(lxw)$. The fluid retention after saturation (frs) is calculated as follows: $frs=(rw-dw)/dw \times 100$. The fluid retention during use (fru) values is a measure, prior to reaching the saturation point, of a material's ability to retain fluid absorbed within the structure when subjected to gravitational stress. The fluid retention during use values reported in Table 1 are determined according to the following protocol.

A sample of the material is placed in a petri dish, and 5 ml of saline is pipetted and dispensed drop lies on to the sample. The saline is allowed to be absorbed into the sample, and its weight (B) is recorded. The sample is then lifted out of the dish with tweezers and held over the dish until

TABLE 1

| Manufacturer | Product | Softness (IFD$_{25}$) N/cm | Support Factor | Conformability (N/cm³) | Fluid Capacity cc/in² | Fluid Cap. Under Compress. (18 mmHg) cc/in² | Fluid Cap. Under Compress. (40 mmHg) cc/in² | Fluid Retention During Use % | Fluid Retention After Saturation % |
|---|---|---|---|---|---|---|---|---|---|
| N/A | Invention | 7.8 | 4.0 | 0.03 | 8.0 | 5.8 | 4.4 | 100% | 98% |
| Avitar | Hydrasorb | 20.9 | 2.5 | 0.04 | 6.3 | 4.1 | 3.0 | 98% | 93% |
| Smith & Nephew | Allevyn | 20.7 | 2.4 | 0.10 | 4.8 | 3.3 | 2.3 | 100% | 92% |
| Ferris | Polymem | 120.5 | 2.2 | 0.16 | 2.7 | 1.8 | 1.4 | 100% | 93% |
| Johnson & Johnson | Sof-Foam | 23.3 | 2.6 | 0.05 | 9.8 | 8.6 | 7.7 | 100% | 94% |
| 3M | 3M Foam | 18.0 | 3.1 | 0.14 | 3.9 | 1.8 | 1.0 | 93% | 92% |
| Molnlycke | Mepilex | 9.4 | 3.8 | 0.03 | 5.3 | 3.0 | 2.1 | 100% | 96% |
| Molnlycke | Mepilex.Lite | 37.9 | 3.7 | 0.031 | 1.7 | 0.7 | 0.5 | — | 88% |
| Medline | Optifoam | 83.8 | 1.9 | 0.22 | 5.0 | 4.1 | 3.6 | 100% | 96% |
| Korean Foam Dressings | Medifoam - F | 127.0 | 1.6 | — | 2.0 | 1.1 | 0.8 | — | 93% |
| Korean Foam Dressings | Medifoam Adhesive | 225.2 | 1.4 | — | 1.4 | 1.0 | 0.7 | — | 89% |
| Korean Foam Dressings | Medifoam Hydrophilic | 61.7 | 2.9 | 0.08 | 3.0 | 2.2 | 1.8 | — | 93% |

The measurement of the softness, support factor and conformability characteristics have been described above. Fluid capacity (fc) is a measure of the total amount of fluid absorbed by a sample of the material at its saturation point. Fluid retention after saturation (frs) is a measure, after reaching the saturation point, of the material's ability to retain fluid absorbed within its structure when subjected to gravitational stress. The fluid capacity and fluid retention after saturation values reported in Table 1 are determined according to the following protocol. First, the length (l) and width (w) dimensions of dry foam samples are measured in inches. The dry weight (dw) of the sample is measured in dripping stops. The dish is then tared-out on the scale, the specimen placed back into the dish and reweighed (C). The fluid retention during use (fru) is then calculated as follows: $fru=(C-B)/B \times 100$.

The fluid capacity (fc) under compression values qualitatively characterizes the fluid handling properties of foam dressings of the present invention compared with other commercially available foam dressings, which is important when the dressing is used in compression therapy systems. Such compression therapy systems are utilized, for example, for the management and treatment of certain types of conditions such as venous insufficiency and related morbidity such as alteration and edema. The fluid capacity under compression values reported in Table 1 by the following protocol. First, the length (l) and width (w) dimensions of dry dressing samples are measured in inches. The dry weight (dw) of the sample is measured in grams. A bath is filled with saline solution, and each of the samples is placed in the saline bath. Using a plate, the sample is compressed and released inside the saline bath three times in succession to remove any air bubbles which may be trapped within the sample, and to force fluid into the matrix of the dressing sample. After 24 hours in the saline bath, the sample is then removed from the bath. Each sample is placed in a petri dish which has openings to permit drainage, and a stainless steel plate measuring approximately 4"×4", is placed over the dressing sample, which is also approximately 4"×4", to stimulate the desired compression force. A plate weighing a proximally 5.6 pounds is used to simulate a pressure of 18 mm Hg, and a plate weighing approximately 12.4 pounds is used to simulate a pressure of 40 mm Hg. The appropriate steel plate is removed from the dressing after 30 minutes, and the wet weight (ww) sample is then measured. The fluid capacity of the sample per unit area is calculated by subtracting the dry weight from the wet weight after compression, and dividing the quantity by the dry area of the specimen tested: $fc=(ww-dw)/(l\times w)=cc/in^2$. Polyurethane foam materials formed according to the principles of the present invention may possess fluid capacity values under compression equivalent to 18 mm Hg of about 4 to about 8 $cc/in^2$, and/or fluid capacity values under compression equivalent to 40 mm Hg of about 3 to about 7 $cc/in^2$. According to alternative embodiments, the polyurethane foam materials formed according to the principles of the present invention may possess fluid capacity values under compression equivalent to 18 mm Hg of about 4.5 to about 6.5 $cc/in^2$, and/or fluid capacity values under compression equivalent to 40 mm Hg of about 4.0 to about 6.0 $cc/in^2$.

As evident from Table 1 above, a polyurethane foam material of the present invention possesses a unique combination of properties which render it especially suitable for use as a dressing material. In particular, the polyurethane foam material the present invention possesses an excellent combination of softness, support and conformability on the one hand, coupled with very good fluid capacity and fluid management characteristics.

Figure 2:
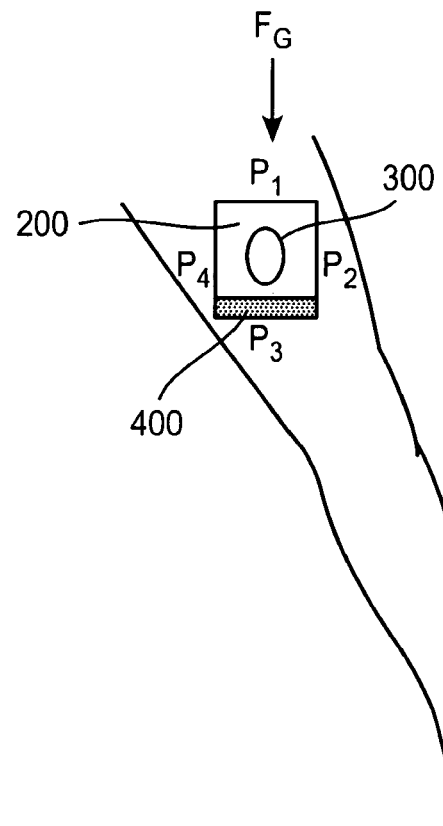
FIG. 2 is a depiction of a super soft pad dressing made with a foam of the present disclosure placed over a wound on the side (sagittal view) of the thigh.
Figure 3:
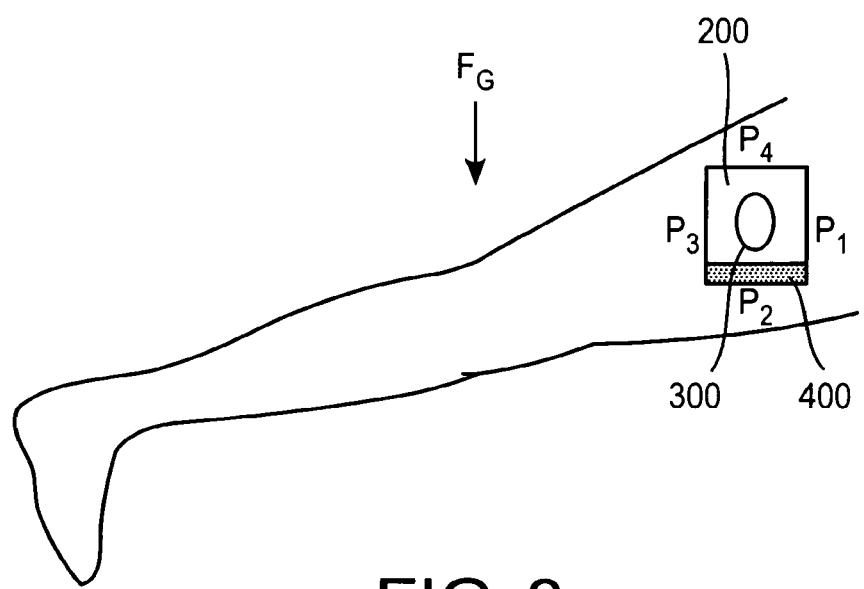
FIG. 3 is an alternate depiction of the super soft pad on the thigh as shown in FIG. 2, wherein the patient is laying on their stomach.
Figure 4:
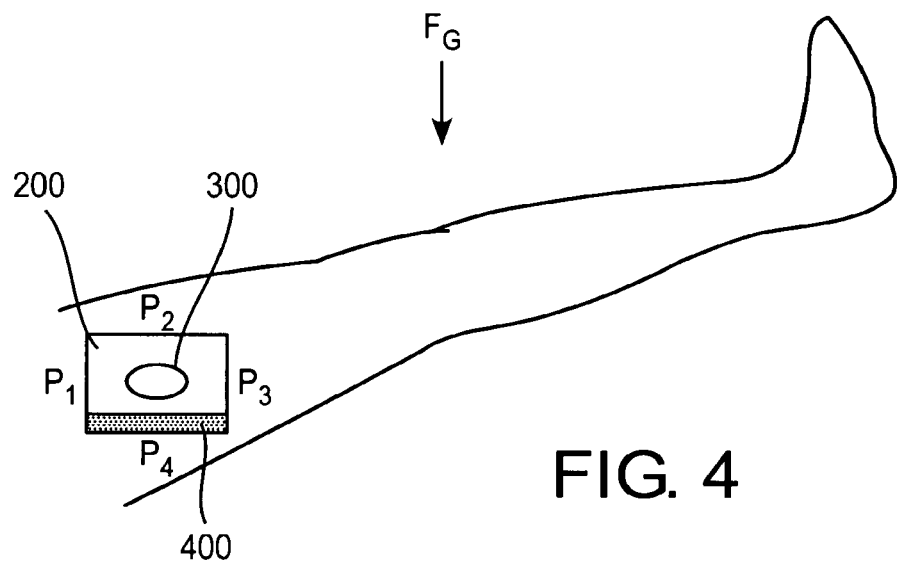
FIG. 4 is an alternate depiction of the super soft pad on the thigh as shown in FIG. 2, wherein the patient is laying on their back.
Figure 5:
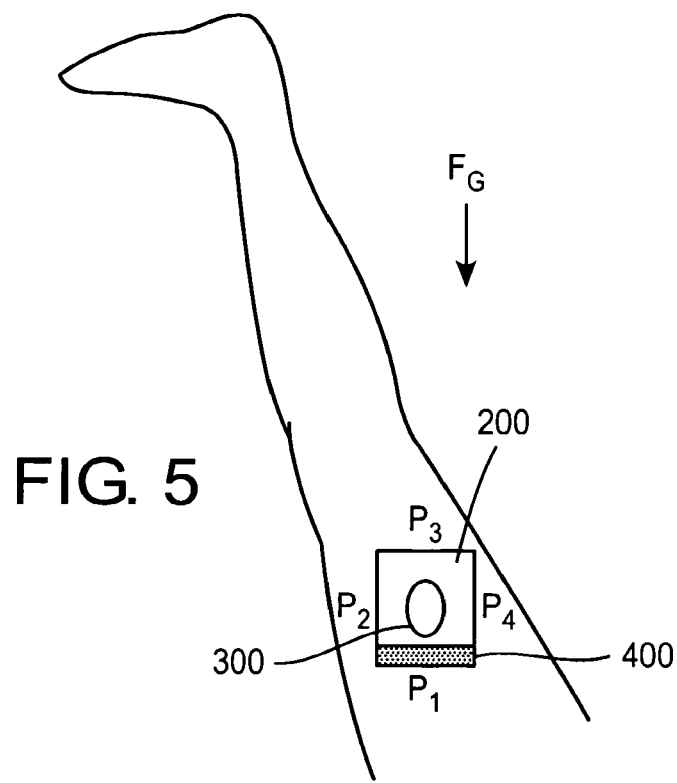
FIG. 5 is an alternate depiction of the super soft pad on the thigh as shown in FIG. 2, wherein the patient is laying on their back with the leg raised, approximating perpendicularity with the torso.
Figure 6:
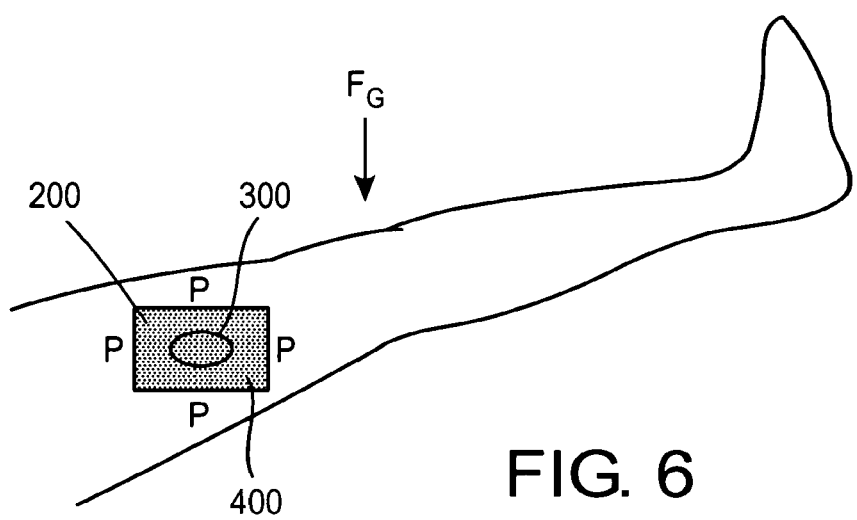
FIG. 6 is an alternate depiction of the super soft pad on the thigh as shown in FIG. 2, wherein the patient is laying on their side such that the foam pad dressing is transversely exposed.

The foam material of the present invention possesses additional fluid management behaviors. For example, where the foam material of the present invention is utilized to form a pad for use as a dressing, up to about 75% of the fluid absorbed into a foam of the present disclosure may migrate and pool at one end of the pad due to the direction and line of action of the force of gravity $F_G$. For example, as depicted in FIG. 2, a pad 200 made of a foam of the present disclosure may be placed over a wound 300 on the side (sagittal view) of the thigh. With the patient in an upright position (that is, standing up), up to about 75% of the fluid 400 in pad 200 may migrate and pool at the $P_3$ position of pad 200 without leaking. Similarly, in FIG. 3, with the same patient laying on their stomach, with the same pad 200 on the same wound 300, up to about 75% of fluid 400 in pad 200 may pool at the $P_2$ position of pad 200 without leaking. FIG. 4 shows the same patient, with the same pad 200 on the same wound 300, laying on their back with up to about 75% of fluid 400 in pad 200 pooling at the $P_4$ position. FIG. 5 shows the same patient with the same pad 200 on the same wound 300, laying on their back with the leg raised perpendicular with the torso, with absorbed fluid 400 proceeding to migrate to the $P_1$ section of pad 200. FIG. 6 shows the same patient with the same pad 200 on the same wound 300, laying on their side such that the foam pad 200 is transversely exposed. Fluid 400 absorbed into the foam matrix in this patient position will evenly distribute throughout pad 200.

The foams of the present disclosure may contain, if desired, one or more medicinal agents. As used herein, "medicinal agent" is used in its broadest sense and includes any substance or mixture of substances that have clinical use. Consequently, medicinal agents may or may not have pharmacological activity per se, e.g., a dye. Examples of classes of medicinal agents which may be combined or mixed into the foam of the present disclosure include antimicrobials, analgesics, antipyretics, anesthetics, antiepileptics, antihistamines, anti-inflammatories, diagnostic agents, sympathomimetics, cholinomimetics, antimuscarinics, antispasmodics, hormones, growth factors, muscle relaxants, antineoplastics, immunosuppressants, steroids, polysaccharides, and enzymes. It is also intended that combinations of medicinal agents may be used.

Suitable antimicrobial agents which may be included as a medicinal agent in the foam of the present disclosure include triclosan, also known as 2,4,4'-trichloro-2'-hydroxydiphenyl ether, chlorhexidine and its salts including chlorhexidine acetate, chlorhexidine gluconate (CHG), chlorhexidine hydrochloride, and chlorhexidine sulfate, biguanides including polyhexamethylne biguanide (PHMB), PHMB derivatives such as polyethylene hexamethylene biguanide (PE-HMB), silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, phosphate glass (optionally in bead form), polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a medicinal agent in the foams of the present disclosure.

Other medicinal agents which may be included as a medicinal agent in the foam of the present disclosure include: local anesthetics; parasympathomimetic agents; tranquilizers; sulfonamides; vaccines; vitamins; antimalarials; anti-migraine agents; anti-parkinson agents such as L-dopa; anti-spasmodics; anticholinergic agents (e.g. oxybutynin); cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antifungals; antivirals; anticoagulants; anticonvulsants; antidepressants; antihistamines; immunological agents; hormones and hormone analogs (e.g., growth hormone, adrenocorticotropic hormone and luteinizing hormone releasing hormone (LHRH)); vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

The amount of medicinal agent present will depend upon the particular medicinal agent chosen, but may be present in any suitable amount. A "suitable amount" is considered to encompass any amount(s) that demonstrate and acceptable level of efficacy, yet is not cytotoxic. For purposes of illustration only, the amount of medicinal agent can vary from about 10 parts per million (ppm) to about 20,000 ppm.

When the medicinal agent is PHMB, or PHMB derivative, the amount added to the foam can be: up to about 20,000 ppm; up to about 17,500 ppm; up to about 15,000 ppm; up to about 12,500 ppm, up to about 10,000 ppm; up to about 9,000 ppm; up to about 7,500 ppm; or up to about 5,000 ppm. According to additional alternative embodiments, the amount of PHMB or PHMB derivative added to the foam can be: up to about 20,000 ppm, and at least about 5,000 ppm; up to about 20,000 ppm, and at least about 7,500 ppm; up to about 20,000 ppm, and at least about 9,000 ppm; up to about 20,000 ppm, and at least about 10,000 ppm; up to about 20,000 ppm, and at least about 12,500 ppm; up to about 20,000 ppm, and at least about 15,000 ppm; or up to about 20,000 ppm, and at least about 17,500 ppm. .

Other additives include tinctures; fillers, for example, carbon black, metal oxides, such as red iron oxide and titanium dioxide, silicates, such as calcium silicates and sodium silicates, acrylic resin powders, various ceramic powders, and the like; softening agents, such as DBP (dibutylphosphate), DOP (dioctylphosphate), TCP (tricresylphosphate), tributoxyethylphosphates, and other esters of various types; and stabilizers, such as trimethyldihydroquinone, phenyl-β-naphthyl amine, p-isopropoxydiphenylamine, diphenyl-p-phenylene diamine, and the like. These additives may be used in amounts of up to 20%, in embodiments from about 0.1% to about 10% by weight of the foam, typically from about 0.5% to about 5% by weight of the foam.

In addition to incorporation into a foam of the present disclosure, medicinal agent(s) or other additives described herein may be incorporated in any other layer of a dressing including a foam of the present disclosure. Such additional layers include, but are not limited to, backing layers and/or adhesive layers as described herein.

Medicinal agent(s) or other additives may be incorporated into the foam or any other layer of a dressing including a foam of the present disclosure by any method within the purview of those skilled in the art. In embodiments, the agent(s) or other additives may be incorporated into the foam by addition of agent(s) or other additives into the aqueous phase before reacting and forming the foam, by separately introducing the agent(s) or additives at the mixing interface, or by a padding process after the foam is cured or after it is dried, for example by applying the agent(s) or additives to the foam by saturating the foam in a trough or similar vessel and then squeezing the saturated foam through pressure rollers to achieve a uniform application of the agent(s) or additives and incorporation of the agent(s) and/or additives both upon the surface of the foam and within the cells of the foam itself. Similar methods may be utilized to incorporate medicinal agent(s) or other additives in other layers of a dressing including the foam, such as a backing layer and/or adhesive layer.

By way of illustrative example, PHMB may be added to the foam matrix by adding it to the aqueous phase mixture prior to mixing with prepolymer to produce the foam. Alternatively, PHMB may be pumped directly to the mixhead through a separate feed line where it is mixed together with the aqueous phase and prepolymer to produce the foam. According to another alternative, the PHMB may be sputter coated at any point in the process from when the aqueous and prepolymer are mixed to any point before drying or after drying of the foam. As a further option, PHMB may be applied to the foam using a metered applicator, preferably a slot applicator, to precisely meter the PHMB onto and into the foam matrix at any point in the process from when the aqueous and prepolymer are mixed to any point before drying or after drying of the foam. According to an additional alternative, PHMB may be added to the foam using a dip and squeeze (padder/nip roll) process at any point from when the aqueous phase and prepolymer are mixed to any point before drying or after drying of the foam.

According to one illustrative example, an aqueous solution comprising polyhexamethylene biguanide (PHMB) mixed with certain surfactants, specifically GLUCOPON® 625 (which is a nonionic alkyl polyglucoside) and EMULGADE® 1000 NI (which is a mixture of cetostearyl alcohol and polyoxyethylene cetyl/stearyl ether) and deionized water. The PHMB is directly incorporated into the foam matrix precursor materials during the polymer mixing stage and the water in the aqueous phase causes foaming to occur. PHMB is commercially available, for example, as Cosmocil® CQ from Arch Chemical.

While not wishing to be bound to any particular theory, addition of PHMB, or derivatives thereof such as PEHMB, during reaction of the foam constituents may result in a covalent attachment via reactive end groups such as amine, guanidine or cyanoguanidine. Under certain conditions, the biguanide molecules may act as crosslinking agents in the creation of a cross-linked polyurethane foam network. Under other conditions, biguanide molecules may become attached to the polyurethane network on one side only. Depending on the conditions present in the reaction, the resulting network may also be a combination of polyurethane and polyurea.

In yet other embodiments, agent(s) or other additives may be applied as a coating to the foams of the present disclosure, either by separate application of said agent(s) or other additives in a solvent and then evaporating the solvent or by their inclusion in an additional layer utilized to form a super-soft pad for use as a wound dressing of the present disclosure. Such layers include those described above as backing layers, including polyurethane backing layers, or any additional nonwoven layer, fibrous layer, or adhesive utilized in combination with a foam of the present disclosure to produce a super soft pad for use as a dressing. In embodiments, agent(s) or additives may be included in a separate coating applied to a foam of the present disclosure when used as a component of a medical dressing, including a pad. Such coatings may be made of any biocompatible material, including both natural and synthetic polymers, copolymers, hydrogels, and the like. Such coatings may also be applied to any backing layer, adhesive layer, or any other layer of a dressing including a foam of the present disclosure.

In embodiments, coating materials may include peptides or proteins including, but not limited to, albumin, collagen, fibrin, elastin and the like. Other coating materials which may be utilized include polysaccharides such as chitosan, alginate, hyaluronic acid and the like. In other embodiments, synthetic polymers may be utilized as the coating material. Such polymers include, for example, polyesters, polyethers, polycarbonates, and polyanhydrides. Suitable polyesters which may be utilized are within the purview of those skilled in the art and include, for example, trimethylene carbonate, ε-caprolactone, p-dioxanone, glycolide, lactide, 1,5-dioxepan-2-one, polybutylene adipate, polyethylene adipate, polyethylene terephthalate, and homopolymers and copolymers thereof. Suitable polyethers which may be utilized are within the purview of those skilled in the art and include, for example, polyethylene glycol, polypropylene glycol, polybutylene glycol, polytetramethylene glycol, polyhexamethylene glycol, homopolymers thereof and copolymers thereof. Suitable polycarbonates include, for example, tetramethylene carbonates, trimethylene carbonates, pentamethylene carbonates, homopolymers thereof, copolymers thereof, and the like.

Foams of the present disclosure and their use in forming dressings, including super-soft pads utilized with dressings, have several advantages over currently available dressings and pads utilized therewith. Many currently available foam dressings are overly firm and/or stiff, which may contribute to overall wound pain and, in some cases, may be the only source of pain to the patient. To the contrary, foams of the present disclosure utilized to form super-soft medical products, such as dressings that possess a softness and a plush and supple surface feel which creates a pleasant sensation to the skin. Thus, dressings including the foams of the present disclosure as super-soft pads or dressings, when used on wounds, enhance patient comfort and help minimize wound pain by not contributing to overall wound pain.

Moreover, the high support factor of the foams of the present disclosure when utilized as a super-soft pad in a dressing further enhances patient comfort at a wound site, when place between body parts, such as between digits, or when used as padding. The high support factor of the foams of the present disclosure also ensures that the pad, when subjected to repeated forces such as patient body weight, does not bottom out.

The high support factor of the foams of the present disclosure also makes their use in a dressing ideal for the treatment of pressure ulcers by relieving pressure at the wound site, thereby allowing the wound to heal. Additionally, for bed-ridden patients, pressure ulcers attributable to long term exposure of intact skin to peak pressures from bony prominences are prevented from occurring.

The high support factor of the foams of the present disclosure also makes this foam pad the most ideal for use to dress under the heel, or under compression systems such as multilayer bandage compression systems, mechanical compression systems provided by bilateral sequential gradient pneumatic compression (SCD), and the like.

The ability of fluid absorbed in the foam matrix to migrate and pool at different sections of the pad based on patient position and the line of action of gravity minimizes exposure of a wound to excessive fluids over long periods of time. The ability of absorbed wound fluid to migrate within the foam matrix may minimize and/or ameliorate further breakdown of peri-wound attributable to maceration of intact skin around wound edges.

In certain embodiments, the superior conformability of the dressings described herein utilizing foams of the present disclosure make it especially useful for dressing wounds located in areas of the human body that may be otherwise difficult to dress with conventional and currently available dressings.

When combined with one or more medicinal agents, foams used as dressing materials have the added benefit of enhanced infection control and wound healing properties.

EXAMPLES

The following Table 2 summarizes the efficacy of the above-described foam materials of the present invention containing PHMB in reducing the levels of various microorganisms according to non-limiting illustrative examples of various embodiments of the present invention.

TABLE 2

| | | | | | Antimicrobial Efficacy Test Method | | | | | |
|---|---|---|---|---|---|---|---|---|---|---|
| | | | PHMB Measured | | Direct Inoculation Method | | 2 inoculation points of $10^6$/point Immersion Method | | 4 inoculation points of 106/point Immersion Method | |
| | | PHMB added in | Non- | | $(0.5 \text{ ml}/10^6)$ | | | | | |
| Run ID | FIG. no | Process ppm | Sterile ppm | Sterile ppm | Sterile | Non Sterile | Sterile | Non Sterile | Sterile | Non Sterile |
| Run 1 | 7 | 5,000 | 2,209 | NA | | YES | | | | |
| Run 2 | 7 | 5,000 | 2,199 | NA | | YES | | | | |
| Run 4 | 7 | 9,000 | 3,846 | NA | | YES | | | | |
| Run 5 | 8 | 7,500 | 3,600~ | NA | | YES | | | | |
| Run 6 | 8-12 | 10,000 | 5,845 | NA | | YES | | | | |
| Run 7 | 8-12 | 10,000 | 5,227 | NA | | YES | | | | |
| Run 11 | 13-15 | 12,500 | 6,720 | 1,874 | | | | YES | | YES |
| Run 12 | 13-15 | 15,000 | 7,780 | 2,280 | | | | YES | | YES |
| Run 13 | 13-15 | 17,500 | 9,724 | 3,229 | | | | YES | | YES |

TABLE 2-continued

Antimicrobial
Efficacy
Test
Method
7 inoculation
points of
106/point
Immersion
Method

| | | Non | Days with Antimicrobial Efficacy | | | | | |
|---|---|---|---|---|---|---|---|---|
| Run ID | Sterile | Sterile | Pseud | Staph. | E. Coli | C. Albic. | E. faecal. | S. Epider. |
| Run 1 | | | | 7** | | | | |
| Run 2 | | | | 7** | | | | |
| Run 4 | | | | 7** | | | | |
| Run 5 | | | | 7* | | | | |
| Run 6 | | | | 7* | 7*** | 7*** | 7*** | 7*** |
| Run 7 | | | | 7* | 7*** | 7*** | 7*** | 7*** |
| Run 11 | YES | | 7*** | | | | | |
| Run 12 | YES | | 7*** | | | | | |
| Run 13 | YES | | 7*** | | | | | |

*at least a 2 log reduction in the number of microorganisms for up to 7 days (a reduction of 2 log or greater is considered a desirable measure of efficacy)
**at least a 5 log reduction in the number of microorganisms for up to 7 days
***at least a 6 log reduction in the number of microorganisms for up to 7 days
~theoretically derived Column 3 of Table 2 represents the amount of PHMB added during that combination of constituent components utilized to make up the foam material of the present invention. As indicated, the amounts reported in Table 2 are in parts per million (ppm). Columns 4 and 5 of Table 2 is representative of the amount of PHMB that is recoverable from the foam dressing, prior to and after sterilization of the dressing material, respectively.

To measure and quantify PHMB in the foam, a High Performance Liquid Chromatography (HPLC) method can be used. The PHMB is extracted from the foam using water and heat. Approximately one gram of foam material is weighed and extracted twice with 150 ml and 100 ml of distilled/deionized water at 65° C. for 30 min. The combined solution is then analyzed by HPLC with the following HPLC conditions; mobile phase: 40% 0.02M HCL/20% methanol/40% water, column: ultrahydrogel 250A, injection size: 50 uL, detector: 215 nm diode array detector.

The values contained in column 5 are representative of the amount of PHMB that is recoverable from the foam dressing after the dressing material has been subjected to a sterilization procedure. As indicated by the values in column 5, sterilization of the dressing can reduce the amount of PHMB in the dressing available to act upon the target microorganisms. As indicated by the lower values of PHMB reported in columns 4 and 5, a certain amount of PHMB that is initially added is used up in the chemical reaction between the constituent components of the foam, and is therefore presumably not available for acting upon the target microorganism(s).

The dressing samples were subjected to two different efficacy testing methodologies.

Antimicrobial Efficacy Test Method 1—Direct Inoculation Testing, 7 Inoculation Points:

Antibacterial activity was assessed in triplicate over a period of 7 days (repeated daily challenge) for foam dressing samples of the present invention containing PHMB. Foam dressings with no PHMB were used as positive controls. The dressings were tested separately against 6 common wound pathogens: *Pseudomonas aeruginosa* American Type Culture Collection (ATCC) #27853, *Staphylococcus epidermidis* ATCC#12228, *Staphylococcus auereus* ATCC#25923, *Escherichia coli* ATCC#25922, *Enterococcus faecalis* ATCC#29212, and *Candida albicans* ATCC#10231. A suspension of each challenge organism was prepared. Dressing samples 25 mm in diameter were placed upon a Trytpic Soy Agar (TSA) bed to maintain moisture and structure (not allowing the dressing to curl). The dressing samples were inoculated with 0.5 ml volume of challenge or target microorganism suspension (6-log cfu/ml) and incubated at 37° C. After 24 hours of incubation, post inoculation, one set of 3 dressings samples was removed and vortexed in 15 ml of Dey-Engley (DE) neutralizing broth. A 1.0 ml sample was extracted from each tube and standard serial dilutions were prepared using DE broth as the diluent. Serial dilution plates were prepared and incubated from 24 hours at 37° C., from which quantification plate counts were performed for total viable counts. The viable counts of test and control samples were compared for the efficacy assessment and recorded in terms of log reduction in the number of microorganisms. The values reported in Table 2, and in the drawing figures, represent the average of the counts of the 3 samples analyzed for microbial activity each day. The remaining dressing samples were reinoculated with challenge organism, incubated for 24 hours, and the next set of 3 dressing samples pulled, vortexed and counted as described above. This procedure was repeated for 7 days.

Antimicrobial Efficacy Test Method 2—Immersion Testing: 2, 4 and 7 Inoculation Points:

25 mm disks of foam material of the present invention containing PHMB, and disks made from the foam of the present invention without PHMB, were prepared in an aseptic manner. The dressings were aseptically transferred into appropriately labeled sterile 50 ml test tubes with a cap. The assay was performed in triplicate for 7 days.

*Pseudomonas aeruginosa* ATCC #27853 was used as the challenge organism. A suspension with *P. aeruginosa* was prepared from fresh colonies on agar plates after overnight incubation and the turbidity was adjusted to 0.5 McFarland standard (~$1.0 \times 10^8$ cfu/ml). The suspension was diluted in Phosphate Buffer Solution (PBS) to yield a final concentration of $1.0 \times 10^8$ cfu/ml. 20 mls of PBS inoculate were added to each test tube with a sample dressing. Positive controls were the above-mentioned foam disks without PHMB, with inoculate suspension. Negative controls were the above-mentioned foam disks without PHMB with PBS only (no inoculate). The test tubes were gently vortexed to ensure saturation of test and control sample dressings. The samples were incubated at 35° C. for 24 hours. Aliquots of 100 μl PBS inoculate were sampled from the test tubes every 24 hours, neutralized in DE neutralizing broth, serially diluted, and plated on TSA plates. Bacterial counts were performed and averaged. Post aliquot removal, the remaining test and positive control samples were re-inoculated with 200 μl of $10^6$ cfu/ml of original inoculate. Negative controls were re-inoculated in the same manner with PBS only. Three different inoculation intervals were performed: (i) 2 points, one initial inoculation and one after 48 hours); (ii) 4 points (initial inoculation and every other day thereafter); and (iii) 7 points (daily inoculations). The bacterial quantification procedure was repeated every 24 hours as described for the remaining time points (7 days) of the assay. The values reported in Table 2, and in the drawing figures, represent the average of the counts of the 3 samples analyzed for microbial activity each day. Bactericidal efficacy was determined as being at least a 2-log reduction when compared to averaged positive control log counts.

As indicated in the far right-hand section of Table 2, dressing materials made from the foam material of the present invention containing the antimicrobial agent PHMB show an effectiveness in reducing the number of microorganisms exposed thereto over a period of at least seven days.

More specific details of the runs reported in Table 2 are contained in FIGS. 7-15.

Figure 7:
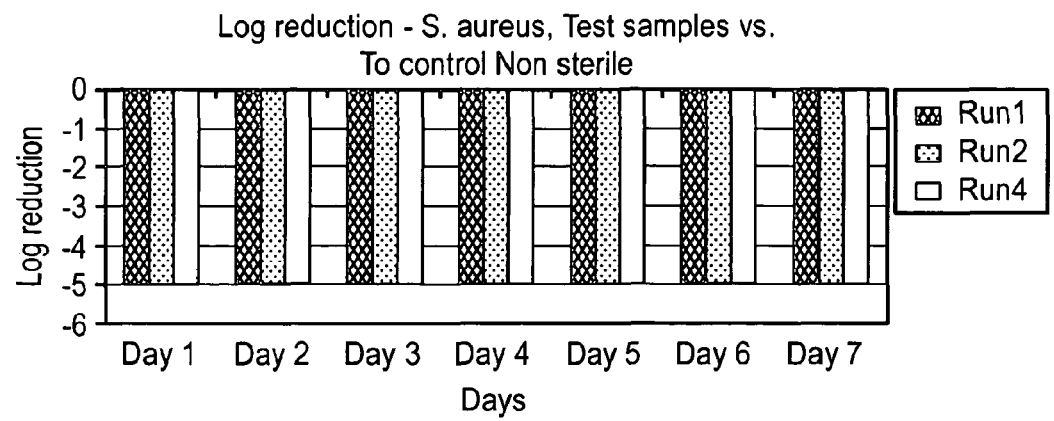
FIG. 7 is a graph illustrating the efficacy of certain embodiments of the present invention with respect to a first target microorganism.

Runs 1, 2 and 4 were conducted utilizing the direct inoculation method described above. In runs 1 and 2, 5,000 ppm of PHMB was added to the foam constituents. In run 4, 9,000 ppm of PHMB was added. Non-sterile dressings were used, and *Staphylococcus auereus* ATCC#25923 was utilized as the target microorganism. As indicated in FIG. 7, the samples in each of the runs showed at least a 5 log reduction in the count of *Staphylococcus auereus* over a seven-day test period.

Figure 8:
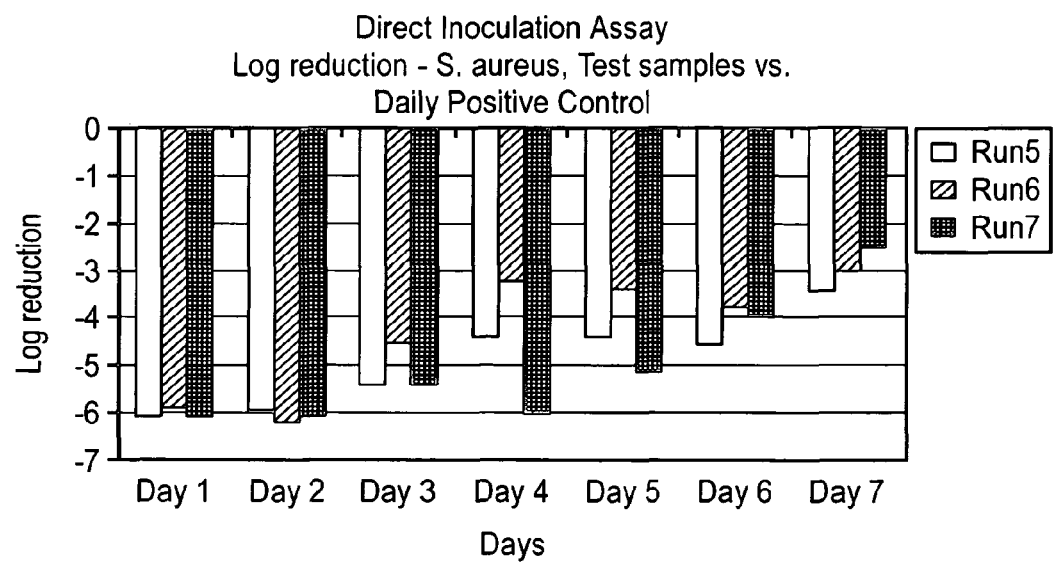
FIG. 8 is a graph illustrating the efficacy of additional embodiments the present invention with respect to the first target microorganism.
Figure 9:
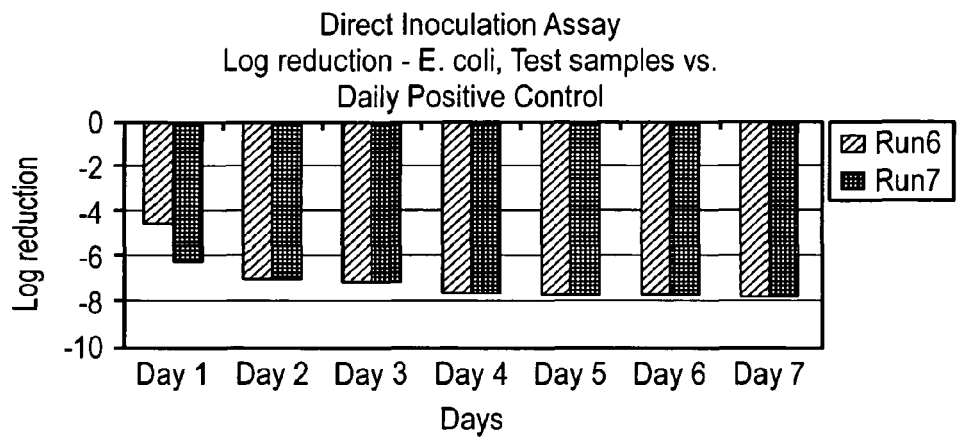
FIG. 9 is a graph illustrating the efficacy of certain embodiments of the present invention with respect to a second target microorganism.
Figure 10:
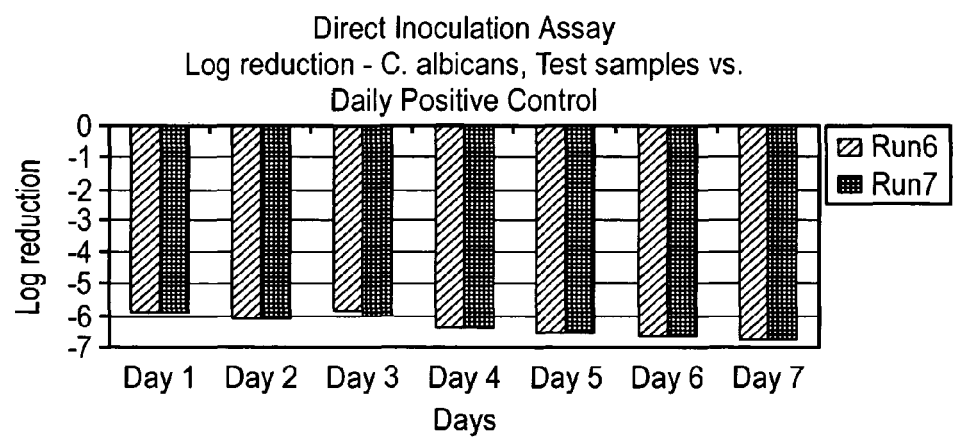
FIG. 10 is a graph illustrating the efficacy of certain embodiments of the present invention with respect to a third target microorganism.
Figure 11:
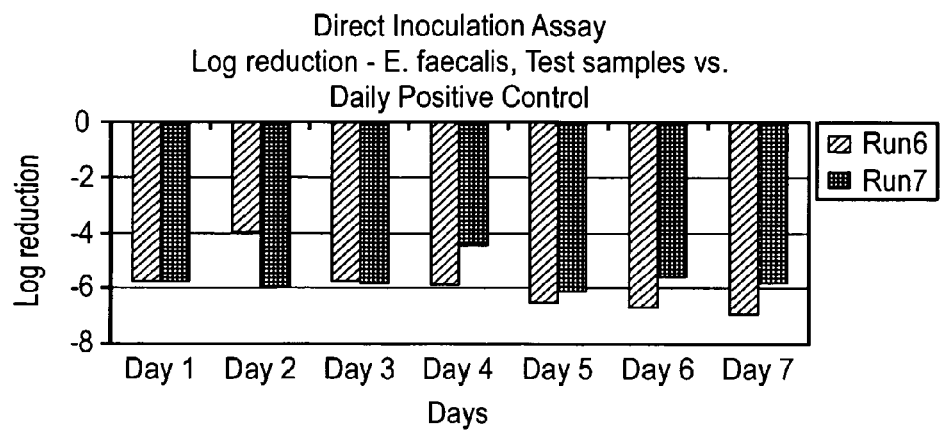
FIG. 11 is a graph illustrating the efficacy of certain embodiments of the present invention with respect to a fourth target microorganism.
Figure 12:
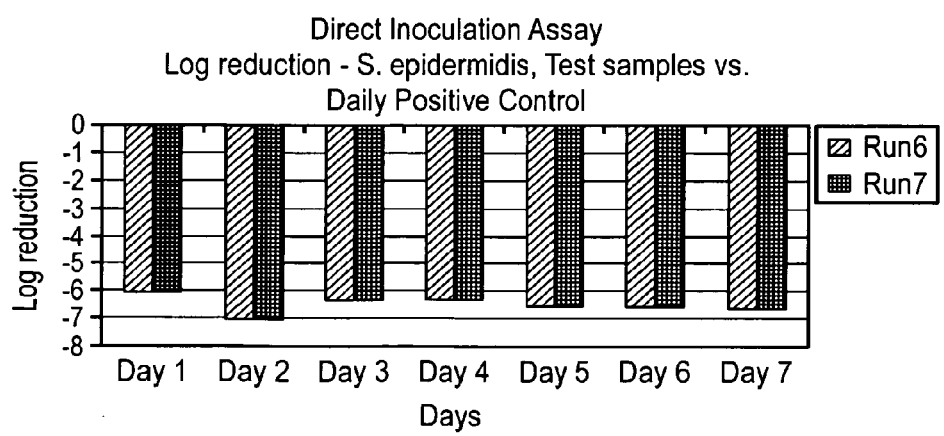
FIG. 12 is a graph illustrating the efficacy of certain embodiments of the present invention with respect to a fifth target microorganism.

Runs 5, 6 and 7 were also conducted utilizing the direct inoculation method described above. In run 5, 7,500 ppm of PHMB was added to the foam constituents. In runs 6 and 7, 10,000 ppm was added in each run. Non-sterile dressings were used, and *Staphylococcus auereus* ATCC#25923 was used as one of the target microorganisms. As indicated in FIG. 8, the samples in runs 5, 6 and 7 were all effective in reducing the count of *Staphylococcus auereus* by more than 2 log over a seven-day period.

Runs 6 and 7 additionally contained samples inoculated with target microorganisms *Escherichia coli* ATCC#25922, *Candida albicans* ATCC#10231, *Enterococcus faecalis* ATCC#29212, and *Staphylococcus epidermidis* ATCC#12228. As illustrated in FIGS. 9-12, the samples were effective in achieving a six log reduction in the counts of each of the above-mentioned microorganisms during a seven-day period as measured relative to a daily positive control.

Figure 13:
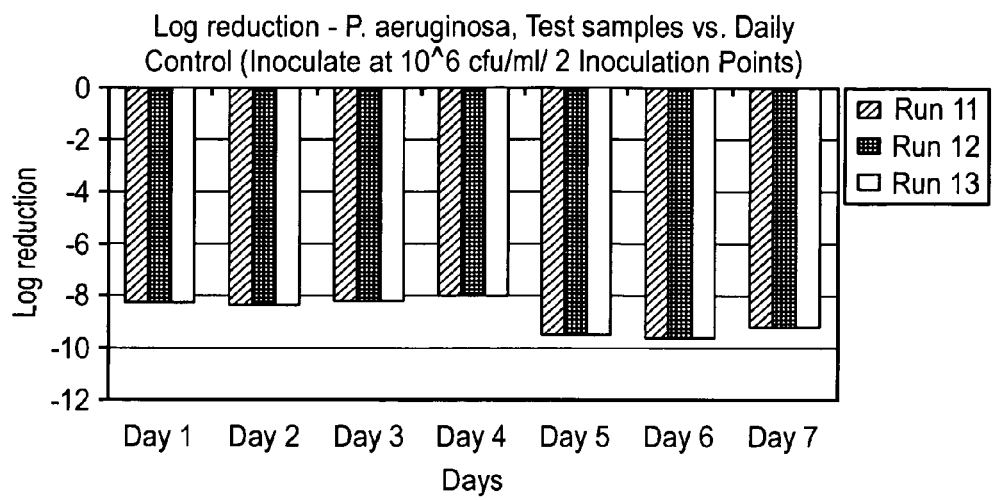
FIG. 13 is a graph illustrating the efficacy of additional alternative embodiments of the present invention with respect to a sixth target microorganism, according to a first inoculation interval.
Figure 14:
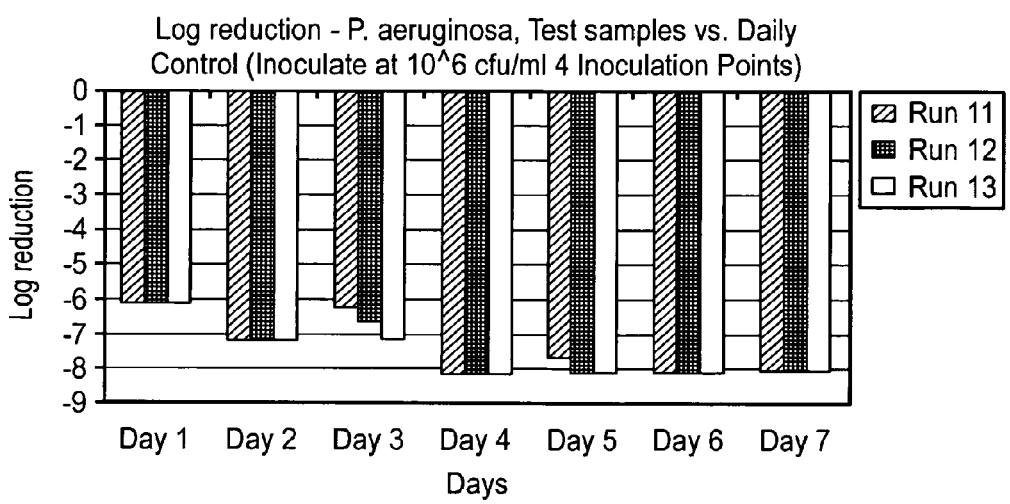
FIG. 14 is a graph illustrating the efficacy of additional alternative embodiments of the present invention with respect to the sixth target microorganism, according to a second inoculation interval.
Figure 15:
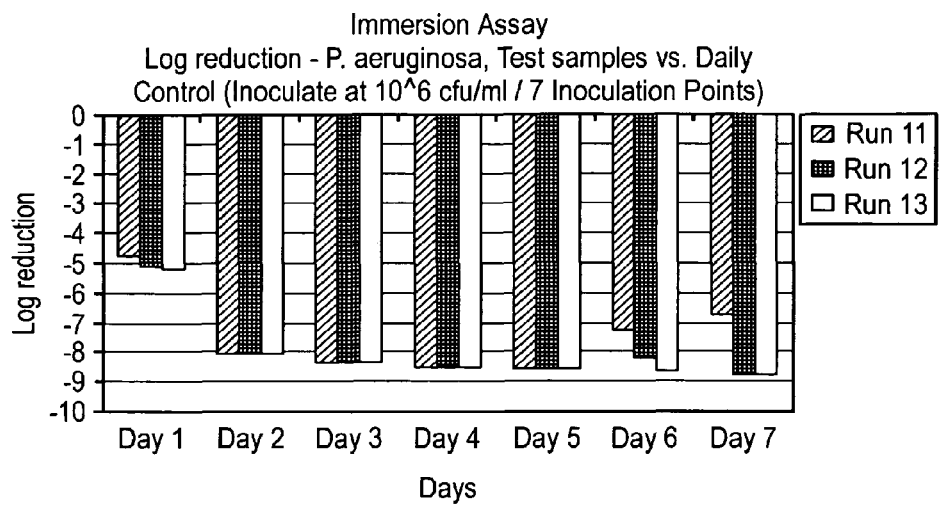
FIG. 15 is a graph illustrating the efficacy of additional alternative embodiments of the present invention with respect to the sixth target microorganism, according to a third inoculation interval.

Runs 11-13 were performed utilizing the above-described immersion method. In run 11, 12,500 ppm of PHMB was added to the foam constituents, in run 12, 15,000 ppm of PHMB was added, and in run 13, 17,500 ppm of PHMB was added. Sterile dressings were used, and *Pseudomonas aeruginosa* ATCC #27853 was used as the target microorganism. Runs 11, 12 and 13 included samples which were inoculated at different intervals. Namely, samples were included which had 2, 4 and 7 inoculation points. As indicated in FIG. 13, samples with 2 inoculation points exhibited at least a 6 log reduction in the count of *Pseudomonas aeruginosa* over a seven-day period. FIG. 14 illustrates that samples with 4 inoculation points also exhibited at least a 6 log reduction in the count of *Pseudomonas aeruginosa* over a seven-day period. Finally, FIG. 15 illustrates that samples with 7 inoculation points also exhibited a 6 log reduction in the count of *Pseudomonas aeruginosa* over a seven-day period (after day 1).

Thus, it is evident from the above that certain embodiments of the present invention, namely, polyurethane based foam is described herein that include the antimicrobial agent PHMB in various amounts, are effective in killing target microorganisms for an extended period of time (i.e., at least 7 days). However, such polyurethane based foam dressings including PHMB have also been observed as providing fast-acting anti-microbial behavior for a broad spectrum of target microorganisms. The following Table 3 summarizes the efficacy of the above-described foam materials of the present invention containing PHMB in quickly reducing the levels of various microorganisms according to non-limiting illustrative examples of various embodiments of the present invention.

TABLE 3

| Run ID | PHMB added in Process | PHMB Measured Non-Sterile | PHMB Measured Sterile | Antimicrobial Efficacy Test Method Direct Inoculation (0.5 ml/$10^6$) St | Antimicrobial Efficacy Test Method Direct Inoculation (0.5 ml/$10^6$) N-St | Antimicrobial Efficacy (Contact Kill): ≥2 log reduction in 10 mins or less Pseud | Staph. | E. Coli | C. Albicans | E. faecalis | S. Epi |
|---|---|---|---|---|---|---|---|---|---|---|---|
| Run 5 | 7,500 | 3,600~ | NA | na | YES | >4 log | >3 log | na | na | na | Na |
| Run 6 | 10,000 | 5,845 | NA | na | YES | >4 log | >2 log | >5 log | 6 log | >4 log | 6 log |
| Run 7 | 10,000 | 5,227 | NA | na | YES | >4 log | >3 log | >5 log | 6 log | 4 log | 6 log |
| Run 11 | 12,500 | 6,720 | 1,874 | YES | na | 4 log | na | na | na | na | na |
| Run 12 | 15,000 | 7,780 | 2,280 | YES | na | 5 log | na | na | na | na | na |
| Run 13 | 17,500 | 9,724 | 3,229 | YES | na | 5 log | na | na | na | na | na |

~Theoretically derived

More specific details of the runs reported in Table 3 are discussed above in connection with the discussion of Table 2. The main difference being that the reduction in the count of the target microorganisms is measured quickly (10 minutes or less) after the initial inoculation.

The efficacy of certain embodiments of the present invention was also tested according to an alternative methodology, commonly referred to as Zone of Inhibition (ZOI) testing. According to this testing technique, a suspension of the target microorganism was prepared as described above in connection with the direct inoculation technique. Specifically, for the illustrated example, a suspension of *Staphylococcus auereus* was prepared. However, instead of inoculating the dressing itself with the suspension, the TSA surface is inoculated with the suspension, and the foam dressing sample containing PHMB is placed over it. As the dressing absorbs fluid from the TSA bed, the boundary of the zone of anti-microbial activity underneath the dressing increases, and extends beyond the borders of the dressing. The dimensions of this zone are measured periodically. The ZOI was observed to have increased in size over time. Without being bound to any particular theory, it is believed that the mechanism behind this increasing zone is that moisture (e.g., exudate) which is initially absorbed from the TSA bed (or wound bed) is eventually released back out of the foam after a certain saturation level (e.g., about 3 to 5 days) and onto the TSA bed carries PHMB from within the foam with it, thereby imparting the observed antimicrobial activity over an increasing zone of inhibition.

Figure 16:
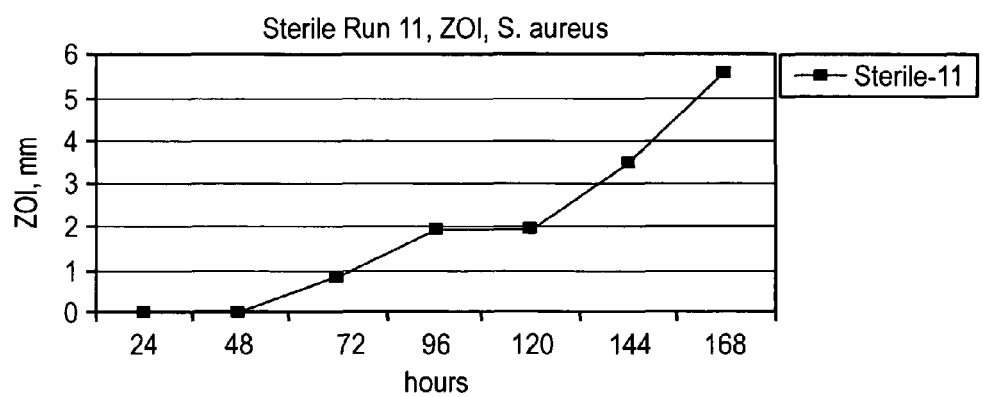
FIG. 16 is a chart comparing the zone of inhibition behavior of an additional alternative embodiment of the present invention over a period of days with respect to the first target microorganism.

FIG. 16 illustrates the results of a zone of inhibition test performed essentially as described above. A sample which is the subject of this analysis comprises a sterile dressing material and a PHMB concentration of 1,874 ppm (see, Table 1, Run 11, sterile sample). The sample illustrated in FIG. 16 exhibits the same behavior explained above with respect to an increasing zone of inhibition observed over time.

Without being bound to any particular theory, it is believed that the above described mechanism by which an increasing ZOI can be produced by dressing materials formed according to the principles of the present invention helps explain the observed high degree of efficacy in eliminating and/or controlling target microorganisms over prolonged periods, i.e., at least seven days.

Again, without being bound to any particular theory, wound dressings constructed according to embodiments of the present invention that contain an anti-microbial agent, such as PHMB, are believed to facilitate wound healing via a number of different mechanisms. First, foam dressings containing an antimicrobial agent, as described herein, act as a barrier that prevents external pathogens for reaching a wound site. Second, as the dressing absorbs fluid from the wound site which is contaminated with pathogens, the anti-microbial agent kills these pathogens within the dressing material in significant number. This helps create an environment at the wound site that prevents and/or reduces or eliminates infection by wound pathogens. Third, it is possible, especially as the dressing reaches its saturation point, that exudate which has been absorbed from the wound site, and subsequently "cleaned" by the reduction in number of pathogens contained therein, can be subsequently eluted from the dressing back into the area of the wound. This eluent can leach anti-microbial agent, such as PHMB, from within the interior of the dressing material and carry it back out into the wound site, thereby promoting reduction in wound pathogens at surfaces of the wound external to the dressing.

To reiterate, the dressing material of the present invention absorbs pathogens in colonized wound fluid. The pathogen count in wound fluid is reduced by 2 log or more in 10 minutes or less. The dressing acts as a barrier to pathogen colonization and proliferation within the dressing. Foam dressings can regurgitate fluid absorbed when compressive forces are applied to the dressing as is the case, several times a day, as a patient moves around in bed or moves around while performing normal daily activities. Thus, there is a repeated absorption of colonized wound fluid into, and desorption of wound fluid with clinically insignificant pathogen count into the wound. In effect, "clean" wound fluid is deposited back into the wound and contaminated fluid is removed. In this manner, the dressing of the present invention facilitates treatment of wound infection by reducing the level of wound bioburden and associated infection.

All numbers expressing quantities or parameters used in the specification are to be understood as being modified in all instances by the term "about". Notwithstanding that the numerical ranges and parameters set forth, the broad scope of the subject matter presented herein are approximations, the numerical values set forth are indicated as precisely as possible. For example, any numerical quantification may inherently contains certain errors resulting from the standard deviation indicative of inaccuracies in their respective measurement techniques.

It will be understood that various modifications may be made to the embodiments disclosed herein. Therefore, the above description should not be construed as limiting, but merely as exemplifications of useful embodiments. Those skilled in the art will envision other modifications within the scope and spirit of the claims appended hereto.

What is claimed is:

1. A medical product comprising:
 a dried, porous foam produced from a composition for a foam comprising:
  at least one NCO-terminated hydrophilic urethane prepolymer comprising a reaction product of at least one isocyanate selected from the group consisting of aromatic isocyanates, aliphatic isocyanates, and combinations thereof, in combination with a polyether polyol comprising a reaction product of an ethylene oxide and a compound containing at least two active hydrogen atoms selected from the group consisting of polyhydric alcohols, polyhydric phenols, amines, polycarboxylic acids, and phosphorous acids;
  an aqueous phase comprising deionized water, at least one fatty alcohol, and at least one alkyl polysaccharide; and
  an antimicrobial agent selected from the group consisting of polyhexamethylene biguanide (PHMB), polyethylene hexamethylene biguanide, and combinations thereof, wherein the antimicrobial agent is present in the composition in an amount up to about 20,000 ppm.

2. The medical product of claim 1, wherein the polyether polyol has an oxyethylene content from about 50% to about 90% by weight and the at least one isocyanate is selected from the group consisting of p-phenylene diisocyanate, 4,4'-diphenylmethane diisocyanate and position isomers thereof, 2,4-toluene diisocyanate and position isomers thereof, 3,4-dichlorophenyl diisocyanate, dicyclohexylmethane-4,4'-diisocyanate, 1,6-hexamethylene diisocyanate and position isomers thereof, isophorone diisocyanate, and combinations thereof.

3. The medical product of claim 1, wherein the at least one fatty alcohol is selected from the group consisting of caproic alcohol, caprylic alcohol, 2-ethylhexyl alcohol, capric alcohol, lauryl alcohol, isotridecyl alcohol, myristyl alcohol, cetyl alcohol, hexyl decanol, palmitoleyl alcohol, stearyl alcohol, cetearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, octyl dodecanol, erucyl alcohol, brassidyl alcohol, coconut oil, and combinations thereof.

4. The medical product of claim 3, wherein the aqueous phase further comprises an ether comprising the reaction product of ethylene oxide with an alcohol selected from the group consisting of caproic alcohol, caprylic alcohol, 2-ethylhexyl alcohol, capric alcohol, lauryl alcohol, isotridecyl alcohol, myristyl alcohol, cetyl alcohol, hexyl decanol, palmitoleyl alcohol, stearyl alcohol, cetearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, octyl dodecanol, behenyl alcohol, erucyl alcohol, brassidyl alcohol, and combinations thereof.

5. The medical product of claim 1, wherein the at least one alkyl polysaccharide comprises a hydrophobic group having from about 8 to about 20 carbon atoms and a polysaccharide hydrophilic group having from about 1.5 to about 10 saccharide units.

6. The medical product of claim 1, wherein the at least one alkyl polysaccharide is selected from the group consisting of glucosides, galactosides, lactosides, fructosides, fructosyls, lactosyls, glucosyls, galactosyls, and mixtures thereof.

7. The medical product of claim 1, wherein the aqueous phase comprises deionized water, cetearyl alcohol, polyoxyethylene ether derived from cetyl alcohol and stearyl alcohol, and an alkyl polyglucoside of the formula:

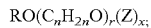

$RO(C_nH_{2n}O)_r(Z)_x$;

wherein Z is derived from glucose, R is a hydrophobic group selected from the group consisting of alkyl, alkylphenyl, hydroxyalkylphenyl, and mixtures thereof having from about 10 to about 18 carbon atoms, n is from about 2 to about 3, r is from about 0 to about 10, and x is from about 1.5 to about 8.

8. The medical product of claim 1, wherein the antimicrobial agent comprises PHMB, wherein the PHMB is present in the composition in an amount between about 5,000 ppm and about 20,000 ppm.

9. The medical product of claim 8, wherein the antimicrobial agent is present in an amount sufficient to provide at least a 2 log reduction in the quantity of one or more common wound pathogens over an exposure period of at least seven days, and wherein the one or more wound pathogens comprise one or more of *Pseudomonas aeruginosa, Staphylococcus epidermidis, Staphylococcus auereus, Escherichia coli, Enterococcus faecalis*, and *Candida albicans*.

10. The medical product of claim 8, wherein the antimicrobial agent is present in an amount sufficient to provide at least a 2 log reduction in the quantity of one or more common wound pathogens after an exposure period of no more than about 10 minutes.

11. The medical product of claim 1, constructed to provide a zone of inhibition upon exposure to one or more wound pathogens that increases after a period of exposure of at least 3 days.

12. The medical product of claim 1, wherein the medical product has an Identation Force Deflection at 25% indentation (IFD 25%) from about 1 pound to about 2 pounds, an Indentation Force Deflection at 65% indentation (IFD 65%) from about 3.5 pounds to about 9 pounds, a support factor from about 3.5 to about 4.5, and a conformability value of from about 0.01 N/cm³ to about 0.1 N/cm³.

13. The medical product of claim 1, wherein the medical product has a fluid capacity under compression equivalent to 18 mm Hg of about 4 to about 8 cc/in².

14. The medical product of claim 1, wherein the medical product has a fluid capacity under compression equivalent to 40 mm Hg of about 3 to about 7 cc/in².

15. The medical product of claim 1, further comprising a backing layer selected from the group consisting of polyurethanes, acetate fibers, acrylic fibers, cellulose ester fibers, modacrylic fibers, polyamide fibers, polyester fibers, polyolefin fibers, polyvinyl alcohol fibers, rayon fibers, polyethylene foam, and combinations thereof.

16. The medical product of claim 1, further comprising a backing layer selected from the group consisting of polyurethanes, polyester fibers, rayon fibers, and combinations thereof, optionally in combination with an adhesive selected from the group consisting of acrylic adhesives, hydrocolloid adhesives, hydrogel adhesives, polyurethane adhesives, and silicone adhesives.

17. The medical product of claim 1, wherein the at least one fatty alcohol is selected from the group consisting of caproic alcohol, caprylic alcohol, 2-ethylhexyl alcohol, capric alcohol, lauryl alcohol, isotridecyl alcohol, myristyl alcohol, cetyl alcohol, hexyl decanol, palmitoleyl alcohol, stearyl alcohol, cetearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, octyl dodecanol, erucyl alcohol, brassidyl alcohol, coconut oil, and combinations thereof, and wherein the at least one alkyl polysaccharide is of the formula:

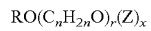

$RO(C_nH_{2n}O)_r(Z)_x$ wherein Z is derived from glucose, R is a hydrophobic group selected from the group consisting of alkyl, alkylphenyl, hydroxyalkylphenyl, and mixtures thereof having from about 10 to about 18 carbon atoms, n is from about 2 to about 3, r is from about 0 to about 10, and x is from about 1.5 to about 8.

18. A wound dressing comprising:
a dried, porous foam formed by a composition comprising:
at least one NCO-terminated hydrophilic urethane prepolymer comprising a reaction product of at least one isocyanate selected from the group consisting of aromatic isocyanates, aliphatic isocyanates, and combinations thereof, in combination with a polyether polyol comprising a reaction product of an ethylene oxide and a compound containing at least two active hydrogen atoms selected from the group consisting of polyhydric alcohols, polyhydric phenols, amines, polycarboxylic acids, and phosphorous acids;
an aqueous phase comprising deionized water, cetearyl alcohol, polyoxyethylene ether derived from cetyl alcohol and stearyl alcohol, and an alkyl polyglucoside of the formula:

$RO(C_nH_{2n}O)_r(Z)_x$;

wherein Z is derived from glucose, R is a hydrophobic group selected from the group consisting of alkyl, alkylphenyl, hydroxyalkylphenyl, and mixtures thereof having from about 10 to about 18 carbon atoms, n is from about 2 to about 3, r is from about 0 to about 10, and x is from about 1.5 to about 8; and from about 5,000 ppm to about 20,000 ppm of an antimicrobial agent comprising polyhexamethylene biguanide.

19. The medical product of claim 18, wherein the foam has an Indentation Force Deflection at 25% indentation (IFD 25%) between about 1 pound to about 2 pounds, and an Indentation Force Deflection at 65% indentation (IFD 65%) between about 3.5 pounds to about 9 pounds.

* * * * *